(12) United States Patent
Ramadoss et al.

(10) Patent No.: US 6,670,345 B1
(45) Date of Patent: Dec. 30, 2003

(54) BETULINIC ACID DERIVATIVES FOR INHABITING CANCER GROWTH AND PROCESS FOR THE MANUFACTURE OF BETULINIC ACID

(75) Inventors: Sunder Ramadoss, New Delhi (IN); Manu Jaggi, Haryana (IN); Mohammad Jamshed Ahmad Siddiqui, Ghaziabad (IN); Achla Behl Khanna, New Deli (IN)

(73) Assignee: Dabur Research Foundation, Sahibabad (IN)

( * ) Notice: Subject to any disclaimer, the term of this patent is extended or adjusted under 35 U.S.C. 154(b) by 0 days.

(21) Appl. No.: 09/431,905

(22) Filed: Nov. 2, 1999

Related U.S. Application Data

(63) Continuation-in-part of application No. 09/040,856, filed on Mar. 18, 1998, now Pat. No. 6,048,847.

(30) Foreign Application Priority Data

Sep. 30, 1997 (IN) ........................................ 2801/DEL/97
Jun. 30, 1999 (IN) ........................................ 932/DEL/99

(51) Int. Cl.[7] ........................... C07J 53/00; A61K 31/56

(52) U.S. Cl. ........................................ 514/169; 552/510

(58) Field of Search ........................... 552/510; 514/169

(56) References Cited

U.S. PATENT DOCUMENTS

| | | | |
|---|---|---|---|
| 5,658,947 A | * 8/1997 | DasGupta et al. | 514/510 |
| 5,679,828 A | * 10/1997 | Lee et al. | 560/116 |
| 5,843,974 A | 12/1998 | Swift | 514/370 |
| 5,869,535 A | 2/1999 | Pezzuto et al. | 514/640 |
| 5,962,527 A | * 10/1999 | Pezzuto et al. | 514/569 |
| 6,214,814 B1 | * 4/2001 | Ramadoss et al. | 514/169 |

FOREIGN PATENT DOCUMENTS

| | | |
|---|---|---|
| JP | 1143832 | 6/1989 |
| WO | 9426695 | 11/1994 |
| WO | 9504526 | 2/1995 |
| WO | 9629068 | 9/1996 |
| WO | 9639033 | 12/1996 |

OTHER PUBLICATIONS

Wrzeciono et al., Triterpene nitrogenous derivatives. VI. 3–and 28–aminolupane derivatives. III. Rocz. Chem. (1972), 46(7/8), 1285–1293. 1972*
Brenner, "Ovulation Inhibition with Nafarel in Acetate Nasal Administration for Six Months", Contraception, 1986.
Choi, Y., "Ellagic Acid Derivatives of Agrostistachys hookeri", Planta medica, 1988, pp. 511–513.
Inoue, H., "Inhibitory Effect of Glycyrrhetinic Acid Derivatives on Lipoxygenase and Prostaglandin Synthease", Chem. Pharm. Bull. vol. 34 (2), pp. 897–901, 1986.
Mosmann, T., "Rapid Colorimetric Assay for Cellular Growth and Survival: Application to Prolieration and Cytoxicity Assays" Journal of Immunlogical Methods, vol. 65., 1983, pp. 55–63.
Pisha, E., "Discovery of Betulinic Acid as a Selective Inhibitor of Human Melanoma that Functions by Induction of Apoptosis" Nature Medicine, vol. 1, No. 10, Oct. 1995, pp. 1046–1051.
Waller, D.P., "In Vitro Spermicidal Activity of gossypol", Contraception, Aug. 1980, vol. 22, No. 2, pp. 183–188.
Yasukawa, "Sterol and Triterpene Derivatives from Plants Inhibit the Effects of a Tumor Promoter, and Sitosterol and Betulinic Acid Inhibit Tumor Formation in Mouse Skin Two–Stage Carcinogenic", Oncology, 46:72–76, 1991.
Delpotre, C.L., "Biological Activities and Metabolites from Trevoa Trinervis Miers", Phytotherapy Research, vol. 11, 504–507 (1997).
Fujioka, et al, Journal of Natural Products, vol. 57, No. 2, Feb. 1, 1994, pp. 243–247.
Hashimoto, et al, Bioorg. Med. Chem., vol. 5, No. 12, 1997, pp. 2133–2143.
Konoshima T. et al., Journal of Natural Products, vol. 50, No. 6, Nov. 1, 1987, pp. 1167–1170.
Miles, D.H., et al., Journal of Pharmaceutical Sciences, vol. 63, No. 4, Apr. 1, 1974, pp. 613–615.
J.S. Lee, et al., Chemical Abstracts + Idexes, vol. 125 No. 19, Nov. 4, 1996, p. 58.
Bishay, D.W. et al., Bulletin of Pharmaceutical Sciences, vol. 10, Part 2, Jan. 1, 1987, pp. 1–20.
Toda, A. et al, Chemical Abstracts, vol. 127, No. 2, Abstract 023542, Jul. 14, 1997.
Pradhan, B.P., et al, Indian J. Chem., Sect. B., vol. 32B, No. 11, pp. 1178–1180.
Patra, A. et al, Chemical Abstracts, vol. 111, No. 9, Abstract 078441, Aug. 28, 1989.
Protiva, J. et al, Collection of Czechoslovak Chemical Communications, vol. 42, No. 4, 1977, pp. 1220–1228.
Protiva, J. et al, Collection of Czechoslovak chemical Communications, vol. 41, No. 4, 1976, pp. 1200–1207.
Protiva, J. et al, Collection of Czechoslovak Chemical Communications, vol. 46, No. 11, 1981, pp. 2734–2741.
Akira Inada, et al., Chemical and Pharmaceutical Bulletin, Vo. 41, No. 3, Mar. 1, 1993, pp. 617–619.
Y. Noda, et al., Chemical and Pharmaceutical Bulletin, vol. 45, No. 10, Jan. 1, 1997, pp. 1665–1670.
Kim, D S H L, et al., Bioorganc & Medical Chemistry Letters, vol. 8, No. 13, Jul. 7, 1998, pp. 1707–1712.

* cited by examiner

*Primary Examiner*—Barbara P. Badio
(74) *Attorney, Agent, or Firm*—Ladas & Parry

(57) ABSTRACT

The invention relates to the use of betulinic acid derivatives for the inhibition and or prevention of cancer growth. The invention also relates to novel betulinic acid derivatives useful for inhibition of tumor cancer cells and a process for the preparation of the derivatives. The invention also relates to anti-leukemic and anti-lymphoma activity of the betulinic acid derivatives, and the use of the derivatives for the treatment of prostate, lung, laryngeal, colon and ovarian cancer.

15 Claims, 3 Drawing Sheets

BETULINIC ACID DERIVATIVES FOR INHABITING CANCER GROWTH AND PROCESS FOR THE MANUFACTURE OF BETULINIC ACID

This is a continuation-in-part of application Ser. No. 09/040,856 filed on Mar. 18, 1998, now U.S. Pat. No. 6,048,847, claims the benefit thereof and incorporates the same by reference.

FIELD OF THE INVENTION

This invention relates to the use of betulinic acid derivatives for the inhibition and or prevention of cancer growth. The invention also relates to novel betulinic acid derivatives useful for inhibition of tumor or cancer cells and a process for the preparation of the derivatives. The invention also relates to anti-leukemic and anti-lymphoma activity of the betulinic acid derivatives, and the use of the derivatives for the treatment of prostate, lung, laryngeal, colon and ovarian cancer.

SUMMARY OF THE INVENTION

The present invention provides for betulinic acid derivatives, methods for preparing betulinic acid derivatives and pharmaceutical compositions comprising betulinic acid derivatives. The derivatives and pharmaceutical compositions comprising betulinic acid derivatives can be used to kill and/or inhibit multiplication of cancer or tumor cells. The bioactivity of the derivatives may be tested using systems normally used by those of skill in the art such as using cultured human leukemia (MOLT-4), lymphoma cells (U937), prostate cancer cells (DU 145), colon cancer cells (HT-29), lung cancer cells (L132), ovarian cancer cells (PA-1) and/or laryngeal cancer cells (HeP.2).

In a preferred embodiment, a pharmaceutically acceptable carrier, diluent, or solvent is used. The invention provides a method of treatment for humans, mammals, or other suffering from cancer or other tumors. The method may suitable comprise, consist of, or consist essentially of administering a therapeutically effective dose of the pharmaceutical composition so as to kill or inhibit the multiplication of cancer or tumor cells. The method of the treatment of the present invention may be particularly useful in the treatment of leukemias and lymphomas and in general in the treatment of prostate, lung, colon and laryngeal cancer.

OBJECT OF THE INVENTION

An object of the invention is to provide a method and composition for inhibiting tumor growth and, particularly, for inhibiting the growth of leukemias and lymphomas and for inhibiting the growth of prostate, colon, larynx, lung and ovarian cancer using betulinic acid, one or more betulinic acid derivatives or a combination thereof.

A further object of the invention is to provide for novel derivatives of betulinic acid and methods for preparing the novel derivatives.

A further object of the invention is to provide a treatment method using betulinic acid derivatives to prevent the growth of cancerous cells, wherein betulinic acid derivative is administered systemically.

A still further object of the invention is to overcome the problem of high toxicity associated with standard chemotherapeutic agents by using a natural product-derived compound, e.g., betulinic acid derivatives.

Yet another object of the invention is to overcome the problem of insufficient availability associated with synthetic anticancer agents by using synthetic derivatives of betulinic acid.

Still another object of the invention is to provide a pharmaceutical formulation containing betulinic acid derivatives, alone or in combination.

BRIEF DESCRIPTION OF THE ACCOMPANYING DRAWINGS

DETAILED DESCRIPTION OF THE INVENTION

Figure 1:
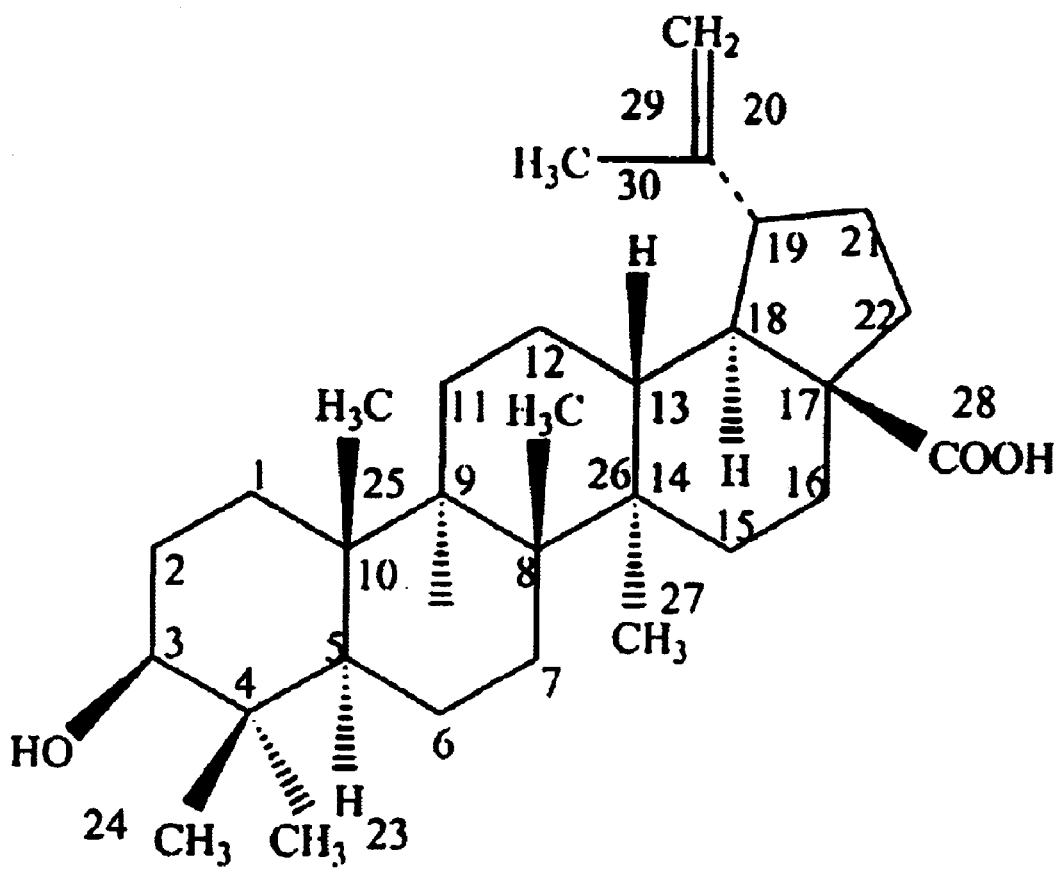
FIG. 1 is the formula representing betulinic acid.
Figure 2:
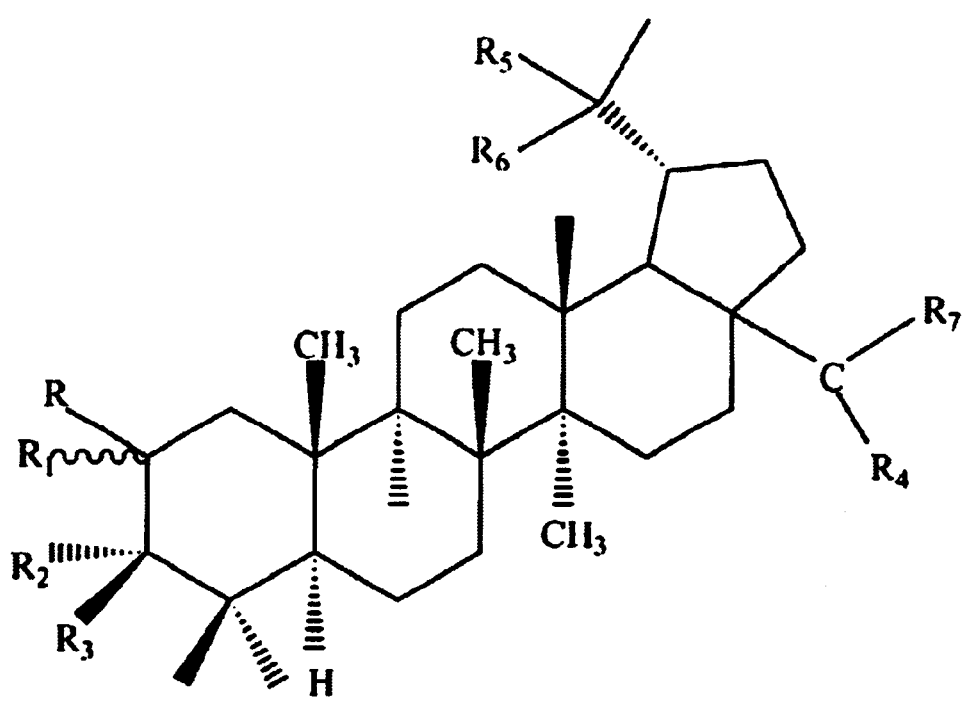
FIG. 2 is a formula representing certain betulinic acid derivatives.
Figure 3:
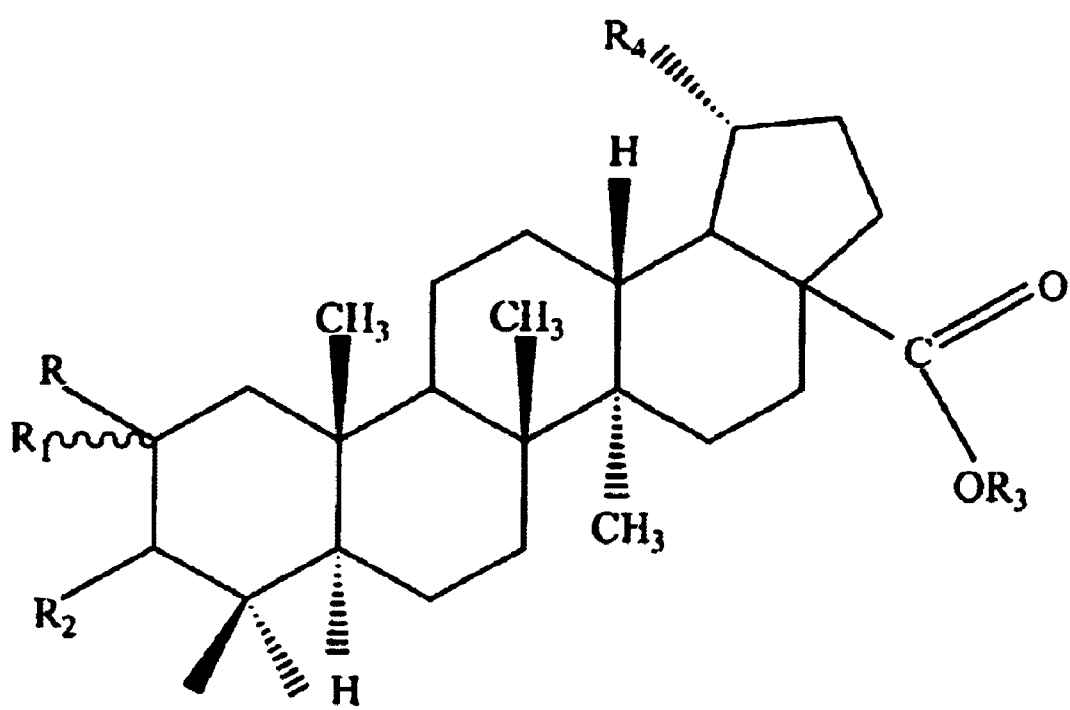
FIG. 3 is a formula representing other betulinic acid derivatives.

The invention relates to novel derivatives of betulinic acid, which may be used for treating a patient with leukemia or lymphoma or prostate, lung, larynx or colon cancer.

The invention also relates to a method of treating a patient with leukemia or lymphoma or prostate, lung, laryngeal, colon or ovarian cancer, said method comprising administering an effective amount of betulinic acid, one or more betulinic acid derivatives or a combination, concurrently or in a mixture to a patient. A patient may be a human, mammal or other animal. The $ED_{50}$ value of active betulinic acid derivatives against leukemia or lymphoma is preferably in the range of 0.3 to 4.0 $\mu$g/ml. The preferred $ED_{50}$ values of active betulinic acid derivatives are in the ranges of 0.4 to 4.0 $\mu$g/ml, 0.5 to 4.0 $\mu$g/ml, 1.0 to 4.0 $\mu$g/ml, 0.35 to 4.0 $\mu$g/ml, 0.50 to 4.0 $\mu$g/ml against prostate, lung, larynx, colon and ovarian cancer respectively.

The structure of betulinic acid is shown in Structure I here below:

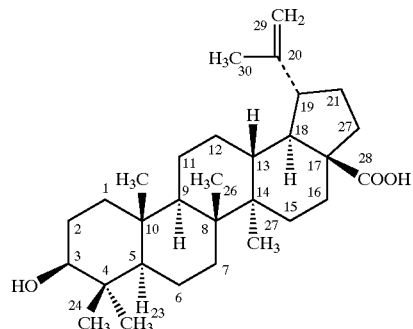

The derivatives of betulinic acid have a basic skeleton of betulinic acid as shown in Structure 2:

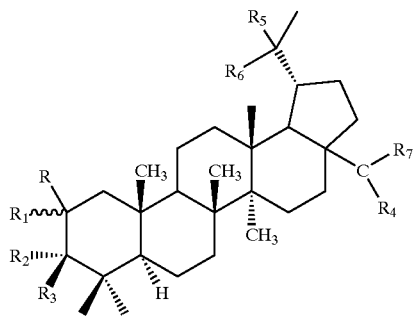

wherein R, $R_1$, $R_2$, $R_3$, $R_4$, $R_5$, $R_6$ and $R_7$ independently or in combination represent the following groups:

R is H;

$R_1$ is H, Br, Cl, F or I;

$R_2$ is H and $R_3$ is OH, OR (R=$C_nH_{2n+1}$ (n=1 to 8), cyclohexyl, phenyl, benzyl, naphthyl or preferably its para substituted derivative), $OCO(CH_2)_nCH_3$ (where n=0 to 14), $OCOC(CH_3)_3$, $OCO(CH_2)_nX$ (where n=1 to 7, X=H, Cl, Br, or F), $OCOC_6H_nX$, $OCOCH_2C_6H_nX$ (n=2 to 4), $OCOC_{10}H_nX$, $OCOCH_2C_{10}H_nX$,(n=2 to 6) (X=H, Cl, Br, F, I, CN, $NO_2$, $NH_2$, $CF_3$, OH, $OCH_3$, $OC_2H_5$, $CHCl_2$ or $C_nH_{2n+1}$ (n=1 to 7)), $OSO_2(CH_2)_nX$ (where n=1 to 7, X=H or Cl), $OSO_2ONH_2$, $OCOC_6H_nX$ (n=0 to 4, X=H, Cl, Br, F, I, CN, $NO_2$, $NH_2$, $CF_3$, OH, $OCH_3$, $OC_2H_5$, $CHCl_2$ or $C_nH_{2n+1}$ (n=1 to 7)), $NH_2$, $NH(CH_2)_nOR$ ((n=2 to 4, R=H or $COCH_3$), NHR, $N(R)^2$ (where R=$CH_3$, $C_2H_5$, $C_3H_7$, or $C_4H_9$), $NHC_6H_nX$, $NHCH_2C_6H_nX$ (where n=2 to 4), $NHCH_2C_{10}H_nX$ (n=2 to 7) (X=H, Cl, Br, F, I, $CHCl_2$, CN, $CF_3$, $CHCl_2$, OH, $OCH_3$, $OC_2H_5$ or $C_nH_{2n+1}$ (n=1 to 7), $RCH_2NOH$ (R=H, $CH_3$, $C_2H_5$,$C_3H_7$, or $C_4H_9$), NHOR (R=H, $COCH_3$, $COC_6H_nX$, $OCH_2C_6H_nX$, or $OC_6H_nX$) (where n=2 to 4, X=Cl, Br, F, I, $CF_3$, $CHCl_2$, CN, $NO_2$, $CH_3$, $NH_2$, OH, $OCH_3$, $OC_2H_5$ or $C_nH_{2n+1}$ (n=1 to 7)), N=$CHC_6H_nX$ (where n=2 to 4), N=$CHC_{10}H_nX$ (n=2 to 6) (X=H, Cl, Br, F, I, $CF_3$, CN, $NO_2$, $NH_2$, OH, $OCH_3$, $OC_2H_5$ or $C_nH_{2n+1}$ (n=1 to 3)), $OCO(CH_2)_nNH_2$ (n=1 to 8), $NHCO(CH_2)_nX$ (X=H, Cl or Br, n=1 to 4), $NHCOC_6H_nX$, $NHCOC_{10}H_nX$ (n=2 to 6), $NHCOCH_2C_6H_nX$ (n=2 to 4), $NHCOCH_2C_{10}H_nX$ (n=2 to 6) (X=Cl, Br, F, I, $CF_3$, CN, $NO_2$, $NH_2$, OH, $OCH_3$, $OC_2H_5$, $CHCl_2$ or $C_nH_{2n+1}$ (n=1 to 7)), $NHCOC_6H_4COOH$, $NHCOC_6H_n(COOH)X$ (where n=2 or 3, X=H, Cl, Br, F, $NO_2$ or $NH_2$), $OCOC_6H_4COOH$, $OCOC_6H_n(COOH)X$ (where n=2 or 3, X=H, Cl, Br, F, $NO_2$ or $NH_2$), $OCOCHRR_1$, (R=H, $CH_3$ or Ph; $R_1$=OH, Cl, Br or $OCOCH_3$), $NHNHC_6H_nX$ (n=2 to 4), $NHNHCH(OH)C_6H_nX$ (n=2 to 4), $NHNHC_{10}H_nX$ (n=2 to 6), NHNHCH(OH)$C_{10}H_nX$ (n=2 to 6) (X=Cl, Br, F, I, OH, $OCH_3$, $OC_2H_5$, $NO_2$, $NH_2$, $CHCl_2$, $CF_3$ or $C_nH_{2n+1}$ (n=1 to 7)), OCOCH=$C(R)^2$ (R is H, $CH_3$ or $C_2H_5$), O—CO—CH=CH—COOH, O—CO—C(Br)=CHCOOH, $OCOCH_2C(R)^2COOH$ (R=H or $CH_3$), $OCO(CH_2)_n$ COOH (n=0 to 3),

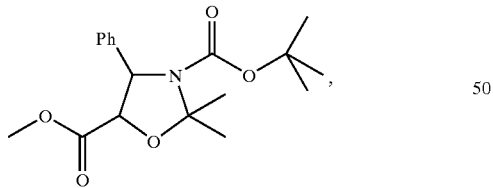

—OOCCH(OH)CH(Ph)R, (R=$NH_2$, $NHC_6H_nX$ (n=2 to 4)), $NHC_{10}H_nX$ (n=2 to 6), $NHCO(CH_2)_nX$ (n=1 to 16) (X=H, Cl, F or Br), $NHCOC_6H_nX$, $NHCOCH_2C_6H_nX$ (n=2 to 4), $NHCOC_{10}H_nX$ (n=2 to 6), N=$CHC_6H_nX$ (n=2 to 4), N=$CHC_{10}H_nX$ (n=2 to 6), $NHCH_2C_6H_nX$ (n=2 to 4), $NHCH_2C_{10}H_nX$ (n=2 to 6) (X=H, Cl, Br, F, I, CN, $NO_2$, $NH_2$, $CF_3$, $CHCl_2$, $OCH_3$, $OC_2H_5$ or $C_nH_{2n+1}$ (n=1 to 7), $NHSO_2(CH_2)_nX$ (n=1 to 7), or $NHSO_2C_6H_nX$ (n=2 to 4) (X=H, Cl, Br, F, $CH_3$, $NO_2$ or $NH_2$);

$R_2$ and $R_3$ together are O, $NNHC_6H_nX$, $NNHCOC_6H_nX$ (n=2 to 4), $NNHC_{10}H_nX$ (n=2 to 6), $NNHCOC_{10}H_nX$ (n=2 to 6), $NC_6H_nX$ (n=2 to 4), $NC_{10}H_nX$ (n=2 to 6), (X=H, Cl, Br, F, I, CN, $NO_2$, $NH_2$, $CF_3$, $CHCl_2$, OH, $OCH_3$, $OC_2H_5$ or $C_nH_{2n+1}$ (n=1 to 7)), $NNHC_6H_nBrX$ (n=2 or 3), (X=F, Cl, $NO_2$, $NH_2$, $OCH_3$, $OC_2H_5$ $C_nH_{2n+1}$ (n=1 to 7)), $NOSO_3H$, N—OX, NHOX (X being H, $CH_3$, $C_2H_5$, $COCH_3$, $SO_2C_6H_4CH_3$, $COC_6H_nX$, $C_6H_nX$, $CH_2C_6H_nX$ (n=2 to 4), (X=H, Cl, Br, F, I, CN, $NO_2$, $NH_2$, OH, $OCH_3$, $OC_2H_5$, $C_nH_{2n+1}$ (n=1 to 7), $CF_3$ or $CHCl_2$), NNHR, (R is $CH_3$, $C_2H_5$, $C_2H_4OY$, (Y=H, alkyl, phenyl, benzyl or its substituted derivative with Cl, Br, F, I, $NO_2$, $NH_2$, $CF_3$, $CHCl_2$, OH, $OCH_3$, $OC_2H_5$ or $C_nH_{2n+1}$ (n=1 to 7));

$R_7$ is O and $R_4$ is H, OH, OM (M=$Na^+$, $K^+$, or $Li^+$), Cl, $N_3$, $NH_2$, OR (R=$CH_3$, $C_2H_5$, $C_3H_7$, or $C_4H_9$), $O(CH_2)_n$ COY (n=1 to 3) (Y=OH, $OCH_3$, $OC_2H_5$, Cl, CN, $N_3$, $NH_2$), $OCH_2CH_2OY$ (Y=H, $CH_3$, $C_2H_5$, $COCH_3$), OCOCH=$C(R)^2$ (R=H, $CH_3$ or $C_2H_5$), $OCO(CH_2)_nX$ (n=1 to 16) (X=H, Cl, F or Br), $OCOC_6H_nX$ (n=0 to 4), $OCOCH_2C_6H_nX$ (n=2 to 4) (X=H, Cl, Br, F, I, CN, $NO_2$, $CF_3$, $CHCl_2$, OH, $OCH_3$, $OC_2H_5$ or $C_nH_{2n+1}$ (n=1 to 7)), $NH(CH_2)_nCH_3$ (n=0 to 9), $NH(CH_2)_nCOOH$ (n=1 to 8), $OCH_2CHO$, $OCH_2CH$=NOX, $OCH_2CH_2NHOX$ (X=H, $CH_3$, $SO_2C_6H_4CH_3$, $OCOCH_3$, $OCOC_6H_5$, phenyl or benzyl substituted derivatives), $OCH_2CH$=$NNHC_6H_nX$, $OCH_2CH_2NHNHC_6H_nX$ (n=2 to 4), $OCH_2CH$=$NNHC_{10}H_nX$ (n=2 to 6), $OCH_2CH_2CH_2NHNHC_{10}H_nX$ (X=H, Cl, Br, F, I, CN, $CF_3$, $CHCl_2$, $NO_2$, $NH_2$, OH, $OCH_3$, $OC_2H_5$ or $C_nH_{2n+1}$ (n=1 to 7), $OCH_2CH_2N(R)^2$ (R is H, $CH_3$, $C_2H_5$, $C_3H_7$, $C_4H_9$, $C_6H_5$, $C_6H_5CH_2$ or its substituted derivative wherein the substituent is selected from Cl, Br, CN, F, I, $NO_2$, $NH_2$, $CF_3$, $CHCl_2$, OH, $OCH_3$, $OC_2H_5$ or $C_nH_{2+1}$ (n=1 to 7)); O-(3-deoxybetulinic acid), O-(3-deoxydihydrobetulinic acid), or O-(2-Bromo-3-oxo-28-oyl-lupane).

$R_4$ is H and $R_7$ is NOH, NHOR, N—OR (R is H, $CH_3$, $C_2H_5$, $SO_2C_6H_4CH_3$, $COCH_3$, $CH_2C_6H_nX$, $COC_6H_nX$ (n=2 to 4), (X=Cl, Br, F, I, CN, $NO_2$, $NH_2$, OH, $OCH_3$, $OC_2H_5$, $CF_3$, $CHCl_2$ or $C_nH_{2n+1}$ (n=1 to 7), $RCH_2NOH$ (R=H, $CH_3$ or $C_2H_5$), $NH_2$, $NHSO_2(CH_2)_nX$ (n=1 to 7), $NHSO_2C_6H_nX$ (n=2 to 5) (X=H, Cl, Br, $CH_3$, $NO_2$ or $NH_2$), $(NR)^2$ (R is H, $CH_3$, $C_2H_5$, $C_3H_7$, $C_4H_9$, phenyl or benzyl or its substituted derivatives), $NC_6H_nX$, $NHC_6H_nX$, N=$CHC_6H_nX$, $NHCH_2C_6H_nX$ (n=2 to 4), $NC_{10}H_nX$, $NHC_{10}H_nX$, N=$CHC_{10}H_nX$, $NHCH_2C_{10}H_nX$ (n=2 to 6) (X=H, Cl, Br, F, I, CN, $NO_2$, $NH_2$, $CF_3$, $CHCl_2$, OH, $OCH_3$, $OC_2H_5$ or $C_nH_{2n+1}$ (n=1 to 7)), $NNHC_6H_nX$, $NHNHC_6H_nX$, NHNHCH(OH)$C_6H_nX$, $NNHCOC_6H_nX$ (n=2 to 4), $NNHC_{10}H_nX$, $NNHCOC_{10}H_nX$, $NHNHC_{10}H_nX$, NHNHCH(OH)$C_{10}H_nX$, (where n=2 to 6, X=H, Cl, Br, F, I, CN, $NO_2$, $NH_2$, OH, $OCH_3$, $OC_2H_5$, $C_nH_{2n+1}$ (n=1 to 7)), NHCOR (R is $CH_3$, $CH_2Cl$, $CHCl_2$, $CCl_3$, $C_2H_5$, $C_2H_4Cl$, $C_3H_7$, $CH_3H_6OH$, $C_3H_6Cl$, $C_6H_5$, $C_6H_nX$, $CH_2C_6H_nX$, $COCH_2C_6H_nX$ (n=2 to 4), $C_{10}H_nX$, $CH_2C_{10}H_nX$, $COCH_2C_{10}H_nX$ (n=2 to 6), X=Cl, Br, CN, F, I, $NO_2$, $NH_2$, $CF_3$, OH, $OCH_3$, $OC_2H_5$, $CHCl_2$ or $C_nH_{2n+1}$ (n=1 to 7));

$R_5$ is H or Br;

$R_6$ is $CH_3$, $CH_2Br$, $CH_2OR$ (R is $CO(CH_2)_nX$, (n=1 to 7; X=H, Cl, Br or F), CHO, CHNOY, $CH_2NHOY$, (Y=H, $CH_3$, $C_2H_5$, $SO_2C_6H_5$, $SO_2C_6H_4CH_3$, $CH_2C_6H_nX$, $C_6H_nX$ (n=2 to 4), X=H, Cl, Br, F, I, CN, $NO_2$, $NH_2$, $CF_3$, $CHCl_2$, OH, $OCH_3$, $OC_2H_5$, $C_nH_{2+1}$ (n=1 to 7)), $RCH_2NOH$ (where R=H, $CH_3$, $C_2H_5$, $C_3H_7$ or $C_4H_9$), $CH_2NH_2$, $CH_2NHR$ or $CH_2N(R)^2$ (R is $CH_3$, $C_2H_5$, $C_3H_7$, $C_4H_9$, $C_6H_5$, $C_6H_nX$, $COC_6H_nX$, or $CH_2C_6H_nX$, $COCH_2C_6H_nX$ (n=2 to 4), $CH_2C_{10}H_nX$, $COC_{10}H_nX$, $COCH_2C_{10}H_nX$ (n=2 to 6), $CH_2OCOC_6H_nX$, $CH_2OCOCH_2C_6H_nX$ (n=2 to 4), $CH_2OCOC_{10}H_nX$, $CH_2OCOCH_2C_{10}H_nX$ (n=2 to 6) (X=H, Cl, Br, F, CN, I, $NO_2$, $NH_2$, OH, $OCH_3$, $OC_2H_5$, $CF_3$, $CHCl_2$, or $C_nH_{2n+1}$ (n=1 to 7)), COOH, COCl, CONHR (R is alkyl or aryl substituted group), CO—OCOR (R is alkyl or aryl substituted group), $COCH_2COR$ (R is OH, $OCH_3$, $OC_2H_5$, $NH_2$ or Cl), $COCH_2CH_2OR$ (R is H, $CO(CH_2)_nX$ (n=1 to 16), $COC_6H_nX$, $COCH_2C_6H_nX$, (n=2 to 4, X=H, Cl, Br, CN, F, I, $NO_2$, $NH_2$, $CF_3$, $CHCl_2$, OH, $OCH_3$, $OC_2H_5$ or $C_nH_{2n+1}$ (n=1 to 7)), $COO(CH_2)_nH$ (n=1 to 5), $COO(CH_2)_nCOY$ (n=1 to 5, Y=OH, $OCH_3$, $OC_2H_5$, Cl or Br), $CH=NC_6H_nX$ (n=2 to 4), $CH=NC_{10}H_nX$ (n=2 to 6), $CH=NNHC_6H_nX$, $CH=NNHCOC_6H_nX$ (n=2 to 4), $CH=NNHC_{10}H_nX$, $CH=NNHCOC_{10}H_nX$ (n=2 to 6), $CH_2NHNHC_6H_4X$ (n=2 to 4), $CH_2NHNHC_{10}H_nX$ (n=2 to 6), $CH_2NHNHCH(OH)C_6H_nX$ (n=2 to 4), $CH_2NHNHCH(OH)C_{10}H_nX$ (n=2 to 6), (where X=H, Cl, Br, F, I, CN, $CF_3$, $NO_2$, $NH_2$, $CHCl_2$, OH, $OCH_3$, $OC_2H_5$ or $C_nH_{2n+1}$ (n=1 to 7));

$R_5$ and $R_6$ together is O, OH, OR (R=$C_nH_{2n+1}$ (n=1 to 8), cyclohexyl, phenyl, benzyl, naphthyl or preferably its parasubstituted derivative), $OCO(CH_2)_nX$ (n=1 to 6, X=H, Cl, or Br), $OCOC_6H_nX$, $OCOCH_2C_6H_nX$ (n=2 to 4, X=H, Cl, Br, F, I, CN, $NO_2$, $NH_2$, $CF_3$, OH, $OCH_3$, $OC_2H_5$ or $C_nH_{2n+1}$ (n=1 to 7)), $OCO(CH_2)_nCOOH$ (n=1 to 3), NOR, NHOR (R=H, $CH_3$, $C_2H_5$, $C_3H_7$, $COCH_3$, $COC_6H_5$, phenyl or benzyl substituted derivatives), $NH_2$, $(NR)^2$ (R=H, $CH_3$, $C_2H_5$, $C_3H_7$, $C_4H_9$, $C_6H_nX$, $CH_2C_6H_nX$; n=2 to 5, X=Cl, Br, F, I, $CF_3$, CN, $NO_2$, $NH_2$, OH, $OCH_3$, $OC_2H_5$, $C_nH_{2n+1}$ (n=1 to 7)), $NHCO(CH_2)_nX$ (n=1 to 16, X=Cl or Br), $NHCOC_6H_nX$, $NHCOCH_2C_6H_nX$ (n=2 to 4), $NHCOC_{10}H_nX$, $NHCOCH_2C_{10}H_nX$ (n=2 to 6) (X=Cl, Br, F, I, CN, $CF_3$, $NO_2$, $NH_2$, OH, $OCH_3$, $OC_2H_5$, $C_nH_{2n+1}$ (n=1 to 7)), $N=CHC_6H_nX$ (n=2 to 4), $N=CHC_{10}H_nX$ (n=2 to 6), $NHCH_2C_6H_nX$ (n=2 to 5), $NHCH_2C_{10}H_nX$ (n=2 to 6), $NNHC_6H_nX$, $NC_6H_nX$, $NHC_6H_nX$ (n=2 to 4), $NC_{10}H_nX$, $NHC_{10}H_nX$, $NNHC_{10}H_nX$, (n=2 to 6), $NNHCOC_6H_nX$, (n=2 to 4), $NNHCOC_{10}H_nX$ (n=2 to 6), NR (R=$C_6H_nX$ (n=2 to 5)), $C_{10}H_nX$ (n=2 to 7) (X=H, Cl, Br, Cl, F, I, CN, $NO_2$, $NH_2$, $CF_3$, $CHCl_2$, $OCH_3$, $OC_2H_5$ or $C_nH_{2n+1}$ (n=1 to 7)).

Preferred compounds are of structure 3:

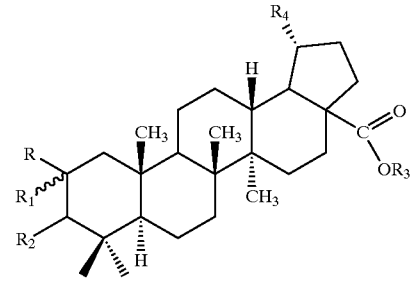

TABLE I

| Derivative | R | $R_1$ | $R_2$ | $R_3$ | $R_4$ |
|---|---|---|---|---|---|
| MJ-321-RS | H | H | —$OCOCH_3$ | H | $CH_2=CCH_3$ |
| MJ-347-RS | H | H | =O | H | $CH_2=CCH_3$ |
| MJ-351-RS | H | H | =NOH | H | $CH_2=CCH_3$ |
| MJ-352-RS | H | Br | =O | H | $BrCH_2C(Br)CH_3$ |
| MJ-353-RS | H | H | =$NNHC_6H_5$ | H | $CH_2=CCH_3$ |
| MJ-398-RS | H | H | —$OCOCH(OCOCH_3)CH_3$ | H | $CH_2=CCH_3$ |
| MJ-408-RS | H | H | —$OCOCH_3$ | —$CH_2COOCH_3$ | $CH_2=CCH_3$ |
| MJ-417-RS | H | H | —OH | —$CH_2COOCH_3$ | $CH_2=CCH_3$ |
| MJ-434-RS | H | H | —$OCOC(CH_3)_3$ | H | $CH_2=CCH_3$ |
| MJ-438-RS | H | H | =NOH | —$CH_2COOCH_3$ | $CH_2=CCH_3$ |
| MJ-443-RS | H | H | —OH | —$CH_2COOCH$ | $CH_2=CCH_3$ |
| MJ-455-RS | H | H | —$OCOCH_3$ | H | —$CH(CH_3)_2$ |
| MJ-457-RS | H | H | —$OCOCH(OCOCH_3)CH_3$ | —$CH_2COOCH_3$ | $CH_2=CCH_3$ |
| MJ-458-RS | H | H | —OH | H | —$CH(CH_3)_2$ |
| MJ-462-RS | H | H | —$OCOCH(OCOCH_3)CH_3$ | H | —$CH(CH_3)_2$ |
| MJ-463-RS | H | H | =NOH | H | —$CH(CH_3)_2$ |
| MJ-481-RS | H | H | =$NOCOCH_3$ | H | $CH_2=CCH_3$ |
| MJ-484-RS | H | H | =$NOSO_2C_6H_4CH_3(4)$ | H | $CH_2=CCH_3$ |
| MJ-524-RS | H | Br | =O | —$CH_2COOCH_3$ | $BrCH_2C(Br)CH_3$ |
| MJ-525-RS | H | H | —$OCOCH(OCOCH_3)CH_3$ | —$CH_2COOCH_3$ | —$CH(CH_3)_2$ |
| MJ-527-RS | H | Br | =O | —$CH_2COOCH_3$ | —$CH(CH_3)_2$ |
| MJ-529-RS | H | H | —$OCOCH_2CH_3$ | H | $CH_2=CCH_3$ |
| MJ-542-RS | H | Br | =O | H | —$CH(CH_3)_2$ |
| MJ-548-RS | H | Br | =O | —$CH_2CH_2COOCH_3$ | —$CH(CH_3)_2$ |
| MJ-577-RS | H | H | —OH | —$CH_2COOH$ | —$CH(CH_3)_2$ |
| MJ-580-RS | H | H | —$OCOC_6H_5$ | H | $CH_2=CCH_3$ |
| MJ-606-RS | H | H | —$OCOC_6H_5$ | H | —$CH(CH_3)_2$ |
| MJ-617-RS | H | H | =$NNHC_6H_4OCH_3(4)$ | H | —$CH(CH_3)_2$ |
| MJ-623-RS | H | H | =$NNHC_6H_4OCH_3(4)$ | H | $CH_2=CCH_3$ |
| MJ-677-RS | H | H | —$NH_2$ | H | $CH_2=CCH_3$ |
| MJ-692-RS | H | H | —$NH_2$ | H | —$CH(CH_3)_2$ |
| MJ-717-RS | H | H | =$NNHC_6H_3Br(3)OCH_3(4)$ | H | —$CH(CH_3)_2$ |
| MJ-719-RS | H | H | =$NNHC_6H_3Br(3)OCH_3(4)$ | H | $CH_2=CCH_3$ |
| MJ-739-RS | H | H | $OCOCH(OCOCH_3)C_6H_5$ | H | $CH_2=CCH_3$ |
| MJ-751-RS | H | H | —$OSO_2CH_3$ | H | $CH_2=C—CH_3$ |
| MJ-784-RS | H | H | $OCOCH(OCOCH_3)C_6H_5$ | H | —$CH(CH_3)_2$ |
| MJ-789-RS | H | H | —$OSO_2CH_3$ | H | —$CH(CH_3)_2$ |

TABLE I-continued

| Derivative | R | $R_1$ | $R_2$ | $R_3$ | $R_4$ |
|---|---|---|---|---|---|
| MJ-790-RS | H | H | —NHCH$_2$CH$_2$OH | H | CH$_2$=CCH$_3$ |
| MJ-807-RS | H | H | =NNHCOC$_6$H$_5$ | H | —CH(CH$_3$)$_2$ |
| MJ-812-RS | H | H | —N=CHC$_6$H$_4$F(4) | H | CH$_2$=CCH$_3$ |
| MJ-813-RS | H | H | =NOCH$_2$C$_6$H$_5$ | H | —CH(CH$_3$)$_2$ |
| MJ-821-RS | H | H | =NNHCH$_2$C$_6$H$_5$ | H | —CH(CH$_3$)$_2$ |
| MJ-826-RS | H | H | =NNHC$_6$H$_4$F(4) | H | CH$_2$=C—CH$_3$ |
| MJ-829-RS | H | H | =NNHC$_6$H$_4$F(4) | H | —CH(CH$_3$)$_2$ |
| MJ-830-RS | H | H | =NHCH$_2$CH$_2$OH | H | —CH(CH$_3$)$_2$ |
| MJ-831-RS | H | H | =NNHCH(OH)C$_6$H$_5$ | H | CH$_2$=C—CH$_3$ |
| MJ-835-RS | H | H | —N=CHC$_6$H$_4$Cl(3) | H | CH$_2$=C—CH$_3$ |
| MJ-839-RS | H | H | —N=CHC$_6$H$_4$NO$_2$(2) | H | —CH(CH$_3$)$_2$ |
| MJ-840-RS | H | H | —N=CHC$_6$H$_4$F(2) | H | —CH(CH$_3$)$_2$ |
| MJ-841-RS | H | H | —N=CHC$_6$H$_4$NO$_2$(3) | H | —CH(CH$_3$)$_2$ |
| MJ-842-RS | H | H | —N=CHC$_6$H$_4$Br(4) | H | —CH(CH$_3$)$_2$ |
| MJ-843-RS | H | H | —OCOC$_6$H$_4$Br(2) | H | CH$_2$=C—CH$_3$ |
| MJ-846-RS | H | H | —OCOC$_6$H$_4$Br(4) | H | —CH(CH$_3$)$_2$ |
| MJ-874-RS | H | Br. | =O | —CH$_2$CH$_2$COOCH$_3$ | —CH(CH$_3$)$_2$ |
| MJ-878-RS | H | H | —NHNHC$_6$H$_5$ | H | —CH(CH$_3$)$_2$ |
| MJ-912-RS | H | H | —NHNHC$_6$H$_4$OCH$_3$(4) | H | —CH(CH$_3$)$_2$ |
| MJ-921-RS | H | H | =NNHC$_6$H$_4$F(2) | H | CH$_2$=C—CH$_3$ |
| MJ-922-RS | H | H | =NNHC$_6$H$_4$F(2) | H | —CH(CH$_3$)$_2$ |
| MJ-926-RS | H | H | —OCOC$_6$H$_3$F$_2$(2,3) | H | CH$_2$=C—CH$_3$ |
| MJ-927-RS | H | H | —OCOC$_6$H$_3$F$_2$(2,3) | H | —CH(CH$_3$)$_2$ |
| MJ-929-RS | H | H | —OCOC$_6$H$_3$F$_2$(3,4) | H | CH$_2$=C—CH$_3$ |
| MJ-931-RS | H | H | —OCOC$_6$H$_3$F$_2$(3,4) | H | —CH(CH$_3$)$_2$ |
| MJ-934-RS | H | H | —OCOC$_6$H$_3$F$_2$(3,5) | H | CH$_2$=C—CH$_3$ |
| MJ-935-RS | H | H | —OCOC$_6$H$_3$F$_2$(3,5) | H | CH$_2$=C—CH$_3$ |
| MJ-936-RS | H | H | —OCOC$_6$H$_3$F$_2$(2,4) | H | CH$_2$=C—CH$_3$ |
| MJ-937-RS | H | H | —OCOC$_6$H$_3$F$_2$(2,4) | H | —CH(CH$_3$)$_2$ |
| MJ-939-RS | H | H | —OCOC$_6$H$_4$CF$_3$(3) | H | CH$_2$=C—CH$_3$ |
| MJ-940-RS | H | H | —OCOC$_6$H$_4$CF$_3$(3) | H | —CH(CH$_3$)$_2$ |
| MJ-942-RS | H | H | —OCOC$_6$H$_4$CF$_3$(2) | H | CH$_2$=C—CH$_3$ |
| MJ-943-RS | H | H | —OCOC$_6$H$_4$CF$_3$(2) | H | —CH(CH$_3$)$_2$ |
| MJ-947-RS | H | H | —OCOC$_6$H$_4$F(2) | H | —CH(CH$_3$)$_2$ |
| MJ-951-RS | H | H | —OCOC$_6$H$_4$F(4) | H | CH$_2$=C—CH$_3$ |
| MJ-952-RS | H | H | —OCOC$_6$H$_4$F(4) | H | —CH(CH$_3$)$_2$ |
| MJ-953-RS | H | H | —OCOC$_6$H$_3$F$_2$(2,3) | CH$_2$COOH$_3$ | CH$_2$=C—CH$_3$ |
| MJ-991-RS | H | H | —N=CHC$_6$H$_4$Cl(2) | H | —CH(CH$_3$)$_2$ |
| MJ-998-RS | H | H | —N=CHC$_6$H$_3$F$_2$(3,4) | H | —CH(CH$_3$)$_2$ |
| MJ-999-RS | H | H | —N=CHC$_6$H$_3$F$_2$(3,5) | H | —CH(CH$_3$)$_2$ |
| MJ-1001-RS | H | H | —NHCH$_2$CH$_2$OCOCH$_3$ | H | —CH(CH$_3$)$_2$ |
| MJ-1002-RS | H | H | —NNHCOC$_6$H$_5$ | H | CH$_2$=C—CH$_3$ |
| MJ-1022-RS | H | H | —NHCOCH$_2$Cl | H | —CH(CH$_3$)$_2$ |
| MJ-1025-RS | H | H | —NHCOCH$_3$ | —CH$_2$COOH$_3$ | —CH(CH$_3$)$_2$ |
| MJ-1027-RS | H | H | —NHCH$_2$CH$_2$OH | —CH$_2$COOH$_3$ | CH$_2$=C—CH$_3$ |
| MJ-1065-RS | H | H | —N=CHC$_6$H$_3$F$_2$(2,4) | H | —CH(CH$_3$)$_2$ |
| MJ-1068-RS | H | H | X | CH$_2$COOCH$_3$ | —CH(CH$_3$)$_2$ |
| MJ-1073-RS | H | H | X | CH$_2$COOCH$_3$ | CH$_2$=C—CH$_3$ |
| MJ-1097-RS | H | H | =NOCH$_2$C$_6$H$_4$NO$_2$(4) | H | CH$_2$=C—CH$_3$ |
| MJ-1098-RS | H | H | =NOCH$_2$C$_6$H$_4$NO$_2$(4) | H | —CH(CH$_3$)$_2$ |
| MJ-1101-RS | H | H | —OH | —COCH=CH$_2$ | CH$_2$=C—CH$_3$ |
| MJ-1103-RS | H | H | —OH | —COCH=CH$_2$ | —CH(CH$_3$)$_2$ |
| MJ-1104-RS | H | H | —OCOC$_6$H$_4$(C$_5$H$_{11}$)(4) | H | CH$_2$=C—CH$_3$ |
| MJ-1105-RS | H | H | OCOC$_6$H$_4$(C$_5$H$_{11}$)(4) | H | —CH(CH$_3$)$_2$ |
| MJ-1108-RS | H | H | OCOCH$_2$C$_6$H$_3$(OCH$_3$)$_2$(2,5) | H | CH$_2$=C—CH$_3$ |
| MJ-1138-RS | H | H | —OCOC$_6$H$_4$(C$_7$H$_{15}$)(4) | H | CH$_2$=C—CH$_3$ |
| MJ-1155-RS | H | Br | =O | 3-deoxy BA(C$_3$) | —CH(CH$_3$)$_2$ |
| MJ-1161-RS | H | Br | =O | Y | —CH(CH$_3$)$_2$ |
| MJ-1163-RS | H | Br. | =O | 2-Bromo-3-oxo-28-oyl lupane | —CH(CH$_3$)$_2$ |
| MJ-1183-RS | H | H | —OCOCH$_2$C$_6$H$_3$(OCH$_3$)$_2$(3,4) | H | CH$_2$=C—CH$_3$ |
| MJ-1187-RS | H | H | =NNHCOC$_6$H$_4$Cl(2) | H | CH$_2$=C—CH$_3$ |
| MJ-1191-RS | H | H | —OCOC$_6$H$_4$(C$_7$H$_{15}$)(4) | H | —CH(CH$_3$)$_2$ |
| MJ-1196-RS | H | H | =NNHC$_6$H$_4$Br(3) | H | CH$_2$=C—CH$_3$ |
| MJ-1197-RS | H | H | OCOCH$_2$C$_6$H$_2$Br(3)(OCH$_3$)$_2$(2,5) | H | —CH(CH$_3$)$_2$ |
| MJ-1198-RS | H | H | =NNHCOC$_6$H$_4$Cl(2) | H | —CH(CH$_3$)$_2$ |
| MJ-1199-RS | H | H | =NNHCOC$_6$H$_4$Br(3) | H | —CH(CH$_3$)$_2$ |
| MJ-1204-RS | H | H | =O | COCH=CH$_2$ | —CH(CH$_3$)$_2$ |
| MJ-1205-RS | H | H | OSO$_2$C$_6$F$_5$ | H | CH$_2$=C—CH$_3$ |
| MJ-1207-RS | H | H | =NNHC$_6$H$_3$Cl$_2$(3,4) | H | CH$_2$=C—CH$_3$ |
| MJ-1210-RS | H | H | =NOH | COCH=CH$_2$ | CH(CH$_3$)$_2$ |
| MJ-1212-RS | H | H | =NNHC$_6$H$_4$Cl(3) | H | CH$_2$=C—CH$_3$ |
| MJ-1213-RS | H | H | —OSO$_2$C$_6$F$_5$ | H | —CH(CH$_3$)$_2$ |
| MJ-1215-RS | H | H | —OCOC$_6$H$_4$(OC$_2$H$_5$)$_2$(4) | H | CH$_2$=C—CH$_3$ |
| MJ-1223-RS | H | H | —OCOC$_6$H$_4$(OC$_2$H$_5$)$_2$(4) | H | —CH(CH$_3$)$_2$ |
| MJ-1237-RS | H | Br. | =NOH | H | —CH(CH$_3$)$_2$ |
| MJ-1245-RS | H | H | —OSO$_2$ONH$_2$ | H | —CH(CH$_3$)$_2$ |

TABLE I-continued

| Derivative | R | R$_1$ | R$_2$ | R$_3$ | R$_4$ |
|---|---|---|---|---|---|
| MJ-1252-RS | H | H | =NNHC$_6$H$_3$Cl$_2$(2,4) | H | CH$_2$=C—CH$_3$ |
| MJ-1253-RS | H | H | =NNHC$_6$H$_3$Cl$_2$(2,5) | H | CH$_2$=C—CH$_3$ |
| MJ-1254-RS | H | H | =NNHC$_6$H$_3$Cl$_2$(2,5) | H | —CH(CH$_3$)$_2$ |
| MJ-1257-RS | H | H | —OSO$_2$ONH$_2$ | H | CH$_2$=C—CH$_3$ |
| MJ-1264-RS | H | Br | —NH$_2$ | H | —CH(CH$_3$)$_2$ |
| MJ-1279-RS | H | H | —OCO(CH$_2$)$_3$NH$_2$ | H | CH$_2$=C—CH$_3$ |
| MJ-1283-RS | H | H | —OCOC$_6$H$_3$(OCH$_3$)$_2$(3,4) | H | —CH(CH$_3$)$_2$ |
| MJ-1286-RS | H | H | —OCOC$_6$H$_3$(OCH$_3$)$_2$(2,4) | H | CH$_2$=C—CH$_3$ |
| MJ-1287-RS | H | H | —OCOC$_6$H$_3$(OCH$_3$)$_2$(2,4) | H | —CH(CH$_3$)$_2$ |
| MJ-1289-RS | H | H | —OCOC(CH$_3$)=C(CH$_3$)COOH | H | —CH(CH$_3$)$_2$ |
| MJ-1295-RS | H | H | —COCClF$_2$ | H | —CH(CH$_3$)$_2$ |
| MJ-1296-RS | H | H | —OCO—C$_6$H$_4$—C$_6$H$_5$ | H | CH$_2$=C—CH$_3$ |
| MJ-1298-RS | H | H | —OCOCH(Cl)C$_6$H$_5$ | H | CH$_2$=C—CH$_3$ |
| MJ-1301-RS | H | H | —OCO(CH$_2$)$_3$COOH | H | —CH(CH$_3$)$_2$ |
| MJ-1304-RS | H | H | —OCOC$_6$H$_4$Cl(4) | H | CH$_2$=C—CH$_3$ |
| MJ-1305-RS | H | H | —OCOC$_6$H$_4$Cl(4) | H | —CH(CH$_3$)$_2$ |
| MJ-1311-RS | H | H | —OSO$_2$C$_6$H$_3$NO$_2$(2)CF$_3$(4) | H | —CH(CH$_3$)$_2$ |
| MJ-1312-RS | H | H | —OSO$_2$CH$_2$CH$_2$Cl | H | CH$_2$=C—CH$_3$ |
| MJ-1313-RS | H | H | —OSO$_2$CH$_2$CH$_2$Cl | H | —CH(CH$_3$)$_2$ |
| MJ-1315-RS | H | H | —OCOC$_6$H$_4$(CHCl$_2$)(3) | H | CH$_2$=C—CH$_3$ |
| MJ-1316-RS | H | H | —OCOC$_6$H$_4$(CHCl$_2$)(3) | H | —CH(CH$_3$)$_2$ |
| MJ-1318-RS | H | H | =NNHCONH$_2$ | H | —CH(CH$_3$)$_2$ |
| MJ-1318-RS | H | H | =NNHCONH$_2$ | H | —CH(CH$_3$)$_2$ |
| MJ-1324-RS | H | H | =NOC$_2$H$_5$ | H | —CH(CH$_3$)$_2$ |
| MJ-1324-RS | H | H | =NOC$_2$H$_5$ | H | —CH(CH$_3$)$_2$ |
| MJ-1326-RS | H | H | =NOCH$_2$C$_6$F$_5$ | H | —CH(CH$_3$)$_2$ |
| MJ-1326-RS | H | H | =NOCH$_2$C$_6$F$_5$ | H | —CH(CH$_3$)$_2$ |
| MJ-1327-RS | H | H | —OCOC$_6$H$_2$COOH(2)Cl$_2$(3,6) | H | CH$_2$=C—CH$_3$ |
| MJ-1328-RS | H | H | —OCOC$_6$H$_2$COOH(2)Cl$_2$(3,6) | H | —CH(CH$_3$)$_2$ |
| MJ-1335-RS | H | H | —OCOCH(Cl)CH$_3$ | H | CH$_2$=C—CH$_3$ |
| MJ-1336-RS | H | H | —OCOCHClCH$_3$ | H | —CH(CH$_3$)$_2$ |
| MJ-1338-RS | H | H | =NNHCOC$_6$H$_4$OH(2) | H | —CH(CH$_3$)$_2$ |
| MJ-1366-RS | H | Br | =N—OCH$_2$C$_6$H$_4$NO$_2$(4) | H | —CH(CH$_3$)$_2$ |
| MJ-1373-RS | H | H | —OSO$_2$C$_6$H$_4$NO$_2$(2) | H | —CH(CH$_3$)$_2$ |
| MJ-1384-RS | H | Br | =NOCH$_2$C$_6$H$_4$NO$_2$(4) | Y | —CH(CH$_3$)$_2$ |
| MJ-1385-RS | H | Br | =NOH | Y | —CH(CH$_3$)$_2$ |
| MJ-1389-RS | H | H | —NHOCH$_2$C$_6$H$_4$NO$_2$(4) | H | —CH(CH$_3$)$_2$ |
| MJ-1396-RS | H | H | —N[COC$_6$H$_3$F$_2$(2,4)]OCH$_2$C$_6$H$_4$NO$_2$(4) | H | —CH(CH$_3$)$_2$ |
| MJ-1396-RS | H | H | —N[COC$_6$H$_3$F$_2$(2,4)]OCH$_2$C$_6$H$_4$NO$_2$(4) | H | —CH(CH$_3$)$_2$ |
| MJ-1399-RS | H | H | —NHCOC$_6$H$_3$F$_2$(2,4) | H | —CH(CH$_3$)$_2$ |
| MJ-1402-RS | H | H | —O-Morpholinoyl | H | —CH(CH$_3$)$_2$ |
| MJ-1403-RS | H | H | —OCOC$_6$H$_2$F$_3$(2,3,6) | H | —CH(CH$_3$)$_2$ |
| MJ-1404-RS | H | H | —OCOC$_6$H$_2$F$_3$(2,3,6) | H | —CH(CH$_3$)$_2$ |
| MJ-1406-RS | H | H | —NHOCH$_2$C$_6$H$_4$NH$_2$(4) | H | —CH(CH$_3$)$_2$ |
| MJ-1407-RS | H | H | —O-Cyclobutanoyl | H | —CH(CH$_3$)$_2$ |
| MJ-1408-RS | H | H | —N[COC$_6$H$_3$F$_2$(2,4)]OCH$_2$C$_6$H$_4$[NHCOC$_6$H$_3$F$_2$(2,4)](4) | H | —CH(CH$_3$)$_2$ |
| MJ-1409-RS | H | H | —OCOC$_6$H$_2$Br(6)F$_2$(2,4) | H | —CH(CH$_3$)$_2$ |
| MJ-1410-RS | H | H | —O-Cyclobutanoyl | H | —CH(CH$_3$)$_2$ |
| MJ-1412-RS | H | H | =NOCH$_2$C$_6$H$_3$Br(2)NO$_2$(4) | H | —CH(CH$_3$)$_2$ |
| MJ-1416-RS | H | H | —O-Cyclohexanoyl | H | —CH(CH$_3$)$_2$ |
| MJ-1417-RS | H | H | —OCOC$_6$H$_2$F$_3$(2,3,5) | H | —CH(CH$_3$)$_2$ |
| MJ-1418-RS | H | H | —NHOCH$_2$C$_6$H$_4$[N=CHC$_6$H$_3$F$_2$(3,4)](4) | H | —CH(CH$_3$)$_2$ |
| MJ-1420-RS | H | H | —NHOCH$_2$C$_6$H$_3$Br(2)NO$_2$(4) | H | —CH(CH$_3$)$_2$ |
| MJ-1421-RS | H | H | —NHOCH$_2$C$_6$H$_2$Br$_2$(3,5)NH$_2$(4) | H | —CH(CH$_3$)$_2$ |
| MJ-1427-RS | H | H | —NHOCH$_2$C$_6$H$_4$[N=CHC$_6$H$_3$F$_2$(2,4)](4) | H | —CH(CH$_3$)$_2$ |
| MJ-1430-RS | H | H | —OCOC$_6$H$_2$Cl(4,5)COOH(2) | H | —CH(CH$_3$)$_2$ |
| MJ-1431-RS | H | H | —OCOC$_6$H$_3$F$_2$(2,4) | Y | —CH(CH$_3$)$_2$ |
| MJ-1437-RS | H | H | =NOH | Y | —CH(CH$_3$)$_2$ |
| MJ-1438-RS | H | H | =NOCH$_2$C$_6$H$_4$NO$_2$(4) | Y | —CH(CH$_3$)$_2$ |
| MJ-1439-RS | H | H | —NHOCH$_2$C$_6$H$_4$NO$_2$(4) | Y | —CH(CH$_3$)$_2$ |
| MJ-1444-RS | H | H | —NH$_2$ | Y | —CH(CH$_3$)$_2$ |
| MJ-1447-RS | H | H | =NNHC$_6$H$_2$Br$_2$(3,5)OCH$_3$(4) | H | —CH(CH$_3$)$_2$ |
| MJ-1448-RS | H | H | —NHOCH$_2$C$_6$H$_4$NH$_2$(4) | H | —CH(CH$_3$)$_2$ |
| MJ-1451-RS | H | H | =NNHC$_6$H$_2$Br$_2$(3,5)OCH$_3$(4) | H | CH$_2$=C—CH$_3$ |
| MJ-1452-RS | H | H | —NHCH$_2$C$_6$H$_3$F$_2$(3,4) | H | —CH(CH$_3$)$_2$ |
| MJ-1453-RS | H | H | —NHCH$_2$C$_6$H$_3$F$_2$(2,4) | H | —CH(CH$_3$)$_2$ |
| MJ-1454-RS | H | H | —NHOCH$_2$C$_6$H$_4$(NHSO$_2$C$_6$F$_5$)(4) | H | —CH(CH$_3$)$_2$ |
| MJ-1455-RS | H | H | —NHOCH$_2$C$_6$H$_4$[NHCH$_2$C$_6$H$_3$F$_2$(2,4)](4) | H | —CH(CH$_3$)$_2$ |
| MJ-1456-RS | H | H | —NHOCH$_2$C$_6$H$_4$[NHCH$_2$C$_6$H$_3$F$_2$(3,4)](4) | H | —CH(CH$_3$)$_2$ |
| MJ-1457-RS | H | H | —NHOCH$_2$C$_6$H$_4$(NHSO$_2$CH$_3$)(4) | H | —CH(CH$_3$)$_2$ |
| MJ-1458-RS | H | H | —NHOCH$_2$C$_6$H$_4$[NHCOC$_6$H$_4$C$_5$H$_{11}$(4)](4) | H | —CH(CH$_3$)$_2$ |
| MJ-1459-RS | H | H | —NHCOC$_6$H$_4$(C$_5$H$_{11}$)(4) | H | —CH(CH$_3$)$_2$ |
| MJ-1460-RS | H | H | —NHSO$_2$C$_6$F$_5$ | H | —CH(CH$_3$)$_2$ |
| MJ-1461-RS | H | H | —NHSO$_2$CH$_3$ | H | —CH(CH$_3$)$_2$ |
| MJ-1462-RS | H | H | —N[COC$_6$H$_3$F$_2$(2,4)]OCH$_2$C$_6$H$_4$[NHCOC$_6$H$_3$F$_2$(2,4)](4) | H | —CH(CH$_3$)$_2$ |
| MJ-1463-RS | H | Br | =NNHC$_6$H$_5$ | H | —CH(CH$_3$)$_2$ |
| MJ-1464-RS | H | Br | =NNHCOC$_6$H$_5$ | H | —CH(CH$_3$)$_2$ |

TABLE I-continued

| Derivative | R | $R_1$ | $R_2$ | $R_3$ | $R_4$ |
|---|---|---|---|---|---|
| MJ-1465-RS | H | Br | =NNHC$_6$H$_4$F(4) | H | —CH(CH$_3$)$_2$ |
| MJ-1466-RS | H | Br | =NNHC$_6$H$_4$(OCH$_3$)(4) | H | —CH(CH$_3$)$_2$ |
| MJ-1467-RS | H | Br | —OH | H | —CH(CH$_3$)$_2$ |
| MJ-1468-RS | H | Br | —OCOC$_6$H$_3$F$_2$(2,4) | H | —CH(CH$_3$)$_2$ |
| MJ-1469-RS | H | Br | —NHOCH$_2$C$_6$H$_4$NH$_2$(4) | H | —CH(CH$_3$)$_2$ |
| MJ-1470-RS | H | Br | —N=CHC$_6$H$_3$F$_2$(3,4) | H | —CH(CH$_3$)$_2$ |
| MJ-1471-RS | H | Br | —NHCH$_2$C$_6$H$_3$F$_2$(3,4) | H | —CH(CH$_3$)$_2$ |
| MJ-1472-RS | H | Br | —N=CHC$_6$H$_3$F$_2$(2,4) | H | —CH(CH$_3$)$_2$ |
| MJ-1473-RS | H | Br | —NHCH$_2$C$_6$H$_3$F$_2$(2,4) | H | —CH(CH$_3$)$_2$ |
| MJ-1474-RS | H | Br | —NHCOC$_6$H$_3$F$_2$(2,4) | H | —CH(CH$_3$)$_2$ |
| MJ-1475-RS | H | Br | —NHSO$_2$CH$_3$ | H | —CH(CH$_3$)$_2$ |
| MJ-1476-RS | H | Br | —NHSO$_2$C$_6$F$_5$ | H | —CH(CH$_3$)$_2$ |
| MJ-1477-RS | H | Br | —OCOC$_6$H$_2$Br(6)F$_2$(2,4) | H | —CH(CH$_3$)$_2$ |
| MJ-1478-RS | H | Br | —NHOCH$_2$C$_6$H$_2$Br$_2$(3,5)NH$_2$(4) | H | —CH(CH$_3$)$_2$ |
| MJ-1479-RS | H | Br | —OCOCH$_3$ | H | —CH(CH$_3$)$_2$ |
| MJ-1480-RS | H | Br | —NHOCH$_2$C$_6$H$_4$NO$_2$(4) | H | —CH(CH$_3$)$_2$ |
| MJ-1481-RS | H | Br | —NHOCH$_2$C$_6$H$_3$Br(2)NO$_2$(4) | H | —CH(CH$_3$)$_2$ |
| MJ-1482-RS | H | Br | —NHOCH$_2$C$_6$H$_4$(NHSO$_2$C$_6$F$_5$)(4) | H | —CH(CH$_3$)$_2$ |
| MJ-1483-RS | H | Br | —NHOCH$_2$C$_6$H$_4$[N=CHC$_6$H$_3$F$_2$(2,4)](4) | H | —CH(CH$_3$)$_2$ |
| MJ-1484-RS | H | Br | —NHOCH$_2$C$_6$H$_4$[NHCH$_2$C$_6$H$_3$F$_2$(2,4)](4) | H | —CH(CH$_3$)$_2$ |
| MJ-1485-RS | H | Br | —NHOCH$_2$C$_6$H$_4$[N=CHC$_6$H$_3$F$_2$(3,4)](4) | H | —CH(CH$_3$)$_2$ |
| MJ-1486-RS | H | Br | —NHOCH$_2$C$_6$H$_4$[NHCH$_2$C$_6$H$_3$F$_2$(3,4)](4) | H | —CH(CH$_3$)$_2$ |
| MJ-1487-RS | H | Br | —NHOCH$_2$C$_6$H$_4$(NHSO$_2$CH$_3$)(4) | H | —CH(CH$_3$)$_2$ |
| MJ-1488-RS | H | Br | —NHOCH$_2$C$_6$H$_4$[NHCOC$_6$H$_4$C$_5$H$_{11}$(4)](4) | H | —CH(CH$_3$)$_2$ |
| MJ-1489-RS | H | H | =NNHC$_6$H$_5$ | Y | —CH(CH$_3$)$_2$ |
| MJ-1490-RS | H | H | =NNHCOC$_6$H$_5$ | Y | —CH(CH$_3$)$_2$ |
| MJ-1491-RS | H | H | =NNHC$_6$H$_4$F(4) | Y | —CH(CH$_3$)$_2$ |
| MJ-1492-RS | H | H | =NNHC$_6$H$_4$(OCH$_3$)(4) | Y | —CH(CH$_3$)$_2$ |
| MJ-1493-RS | H | H | —NHOCH$_2$C$_6$H$_4$(NHSO$_2$C$_6$F$_5$)(4) | Y | —CH(CH$_3$)$_2$ |
| MJ-1494-RS | H | H | —NHOCH$_2$C$_6$H$_4$[N=CHC$_6$H$_3$F$_2$(2,4)](4) | Y | —CH(CH$_3$)$_2$ |
| MJ-1495-RS | H | H | —NHOCH$_2$C$_6$H$_4$[NHCH$_2$C$_6$H$_3$F$_2$(2,4)](4) | Y | —CH(CH$_3$)$_2$ |
| MJ-1496-RS | H | H | —NHOCH$_2$C$_6$H$_4$[N=CHC$_6$H$_3$F$_2$(3,4)](4) | Y | —CH(CH$_3$)$_2$ |
| MJ-1497-RS | H | H | —NHOCH$_2$C$_6$H$_4$[NHCH$_2$C$_6$H$_3$F$_2$(3,4)](4) | Y | —CH(CH$_3$)$_2$ |
| MJ-1498-RS | H | H | —NHOCH$_2$C$_6$H$_4$(NHSO$_2$CH$_3$)(4) | Y | —CH(CH$_3$)$_2$ |
| MJ-1499-RS | H | H | —NHOCH$_2$C$_6$H$_4$[NHCOC$_6$H$_4$C$_5$H$_{11}$(4)](4) | Y | —CH(CH$_3$)$_2$ |
| MJ-1500-RS | H | H | —N=CHC$_6$H$_3$F$_2$(3,4) | Y | —CH(CH$_3$)$_2$ |
| MJ-1501-RS | H | H | —NHCH$_2$C$_6$H$_3$F$_2$(3,4) | Y | —CH(CH$_3$)$_2$ |
| MJ-1502-RS | H | H | —N=CHC$_6$H$_3$F$_2$(2,4) | Y | —CH(CH$_3$)$_2$ |
| MJ-1503-RS | H | H | —NHCH$_2$C$_6$H$_3$F$_2$(2,4) | Y | —CH(CH$_3$)$_2$ |
| MJ-1504-RS | H | H | —NHCOC$_6$H$_3$F$_2$(2,4) | Y | —CH(CH$_3$)$_2$ |
| MJ-1505-RS | H | H | —NHSO$_2$CH$_3$ | Y | —CH(CH$_3$)$_2$ |
| MJ-1506-RS | H | H | —NHSO$_2$C$_6$F$_5$ | Y | —CH(CH$_3$)$_2$ |
| MJ-1507-RS | H | H | —NHOCH$_2$C$_6$H$_2$Br$_2$(3,5)NH$_2$(4) | Y | —CH(CH$_3$)$_2$ |
| MJ-1508-RS | H | H | —OCOCH$_3$ | Y | —CH(CH$_3$)$_2$ |
| MJ-1509-RS | H | H | —N[COC$_6$H$_3$F$_2$(2,4)]OCH$_2$C$_6$H$_4$[NHCOC$_6$H$_3$F$_2$(2,4)](4) | Y | —CH(CH$_3$)$_2$ |
| MJ-1510-RS | H | H | —N[COC$_6$H$_3$F$_2$(2,4)]OCH$_2$C$_6$H$_4$NO$_2$(4) | Y | —CH(CH$_3$)$_2$ |
| MJ-1511-RS | H | H | —NHOCH$_2$C$_6$H$_3$Br(2)NO$_2$ | Y | —CH(CH$_3$)$_2$ |
| MJ-1512-RS | H | Br | =NNHC$_6$H$_5$ | Y | —CH(CH$_3$)$_2$ |
| MJ-1513-RS | H | Br | =NNHCOC$_6$H$_5$ | Y | —CH(CH$_3$)$_2$ |
| MJ-1514-RS | H | Br | =NNHC$_6$H$_4$F(4) | Y | —CH(CH$_3$)$_2$ |
| MJ-1515-RS | H | Br | =NNHC$_6$H$_4$(OCH$_3$)(4) | Y | —CH(CH$_3$)$_2$ |
| MJ-1516-RS | H | Br | —OH | Y | —CH(CH$_3$)$_2$ |
| MJ-1517-RS | H | Br | —OCOC$_6$H$_3$F$_2$(2,4) | Y | —CH(CH$_3$)$_2$ |
| MJ-1518-RS | H | Br | —NHOCH$_2$C$_6$H$_4$NH$_2$(4) | Y | —CH(CH$_3$)$_2$ |
| MJ-1519-RS | H | Br | —NH$_2$ | Y | —CH(CH$_3$)$_2$ |
| MJ-1520-RS | H | Br | —N=CHC$_6$H$_3$F$_2$(3,4) | Y | —CH(CH$_3$)$_2$ |
| MJ-1521-RS | H | Br | —NHCH$_2$C$_6$H$_3$F$_2$(3,4) | Y | —CH(CH$_3$)$_2$ |
| MJ-1522-RS | H | Br | —N=CHC$_6$H$_3$F$_2$(2,4) | Y | —CH(CH$_3$)$_2$ |
| MJ-1523-RS | H | Br | —NHCH$_2$C$_6$H$_3$F$_2$(2,4) | Y | —CH(CH$_3$)$_2$ |
| MJ-1524-RS | H | Br | —NHCOC$_6$H$_3$F$_2$(2,4) | Y | —CH(CH$_3$)$_2$ |
| MJ-1525-RS | H | Br | NHSO$_2$CH$_3$ | Y | —CH(CH$_3$)$_2$ |
| MJ-1526-RS | H | Br | NHSO$_2$C$_6$F$_5$ | Y | —CH(CH$_3$)$_2$ |
| MJ-1527-RS | H | Br | —OCOC$_6$H$_2$Br(6)F$_2$(2,4) | Y | —CH(CH$_3$)$_2$ |
| MJ-1528-RS | H | Br | —NHOCH$_2$C$_6$H$_2$Br$_2$(3,5)NH$_2$(4) | Y | —CH(CH$_3$)$_2$ |
| MJ-1529-RS | H | Br | —OCOCH$_3$ | Y | —CH(CH$_3$)$_2$ |
| MJ-1530-RS | H | Br | —NHOCH$_2$C$_6$H$_4$NO$_2$(4) | Y | —CH(CH$_3$)$_2$ |
| MJ-1531-RS | H | Br | —NHOCH$_2$C$_6$H$_4$Br(2)NO$_2$ | Y | —CH(CH$_3$)$_2$ |
| MJ-1532-RS | H | Br | —NHOCH$_2$C$_6$H$_4$(NHSO$_2$C$_6$F$_5$)(4) | Y | —CH(CH$_3$)$_2$ |
| MJ-1533-RS | H | Br | —NHOCH$_2$C$_6$H$_4$[N=CHC$_6$H$_3$F$_2$(2,4)](4) | Y | —CH(CH$_3$)$_2$ |
| MJ-1534-RS | H | Br | —NHOCH$_2$C$_6$H$_4$[NHCH$_2$C$_6$H$_3$F$_2$(2,4)](4) | Y | —CH(CH$_3$)$_2$ |
| MJ-1535-RS | H | Br | —NHOCH$_2$C$_6$H$_4$[N=CHC$_6$H$_3$F$_2$(3,4)](4) | Y | —CH(CH$_3$)$_2$ |
| MJ-1536-RS | H | Br | —NHOCH$_2$C$_6$H$_4$[NHCH$_2$C$_6$H$_3$F$_2$(3,4)](4) | Y | —CH(CH$_3$)$_2$ |
| MJ-1537-RS | H | Br | —NHOCH$_2$C$_6$H$_4$(NHSO$_2$CH$_3$)(4) | Y | —CH(CH$_3$)$_2$ |
| MJ-1538-RS | H | Br | —NHOCH$_2$C$_6$H$_4$[NHCOC$_6$H$_4$C$_5$H$_{11}$(4)](4) | Y | —CH(CH$_3$)$_2$ |

TABLE I-continued

| Derivative | R | $R_1$ | $R_2$ | $R_3$ | $R_4$ |
|---|---|---|---|---|---|
| MJ-1539-RS | H | Br | —N[$COC_6H_3F_2(2,4)$]$OCH_2C_6H_4$[$NHCOC_6H_3F_2(2,4)$](4) | Y | —$CH(CH_3)_2$ |
| MJ-1540-RS | H | Br | —N[$COC_6H_3F_2(2,4)$]$OCH_2C_6H_4NO_2$(4) | Y | —$CH(CH_3)_2$ |

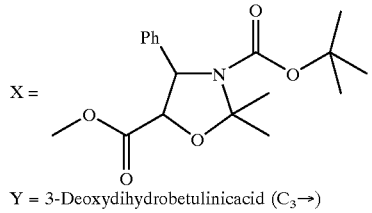

X =

Y = 3-Deoxydihydrobetulinicacid ($C_3 \rightarrow$)

The invention also relates to methods of preparing the novel compounds and in the examples below the term "substrate" refers to betulinic aid, dihydrobetulinic acid or their derivatives as starting material unless otherwise indicated. Dihydrobetulinic acid is obtained from betulinic acid by reduction of $C_{20-29}$ double bond, whereas dihydrobetulinic acid derivatives refer to its derivatization at either $C_2$, $C_3$, $C_{20}$, $C_{28}$ and $C_{29}$ positions.

Conventional procedures known to those skilled in the art can be used in the preparation of the various betulinic acid derivatives wherein the starting material is betulinic acid or a derivative thereof unless otherwise specifically mentioned.

The compositions of the invention may contain one or more derivatives of betulinic acid or betulinic acid in combination with one or more derivatives of betulinic acid.

The compositions of this invention may contain physiologically acceptable diluents, fillers, lubricants, excipients, solvents, binders, stabilizers, and the like. Diluents that may be used in the compositions include but are not limited to dicalcium phosphate, calcium sulphate, lactose, cellulose, kaolin, mannitol, sodium chloride, dry starch, powdered sugar and for extended release tablet-hydroxypropyl methyl cellulose (HPMC). The binders that may be used in the compositions include but are not limited to starch, gelatin and fillers such as sucrose, glucose, dextrose and lactose.

Natural and synthetic gums that may be used in the compositions include but are not limited to sodium alginate, ghatti gum, carboxymethyl cellulose, methyl cellulose, polyvinyl pyrrolidone and veegum. Excipients that may be used in the compositions include but are not limited to microcrystalline cellulose, calcium sulfate, dicalcium phosphate, starch, magnesium stearate, lactose, and sucrose. Stabilizers that may be used include but are not limited to polysaccharides such as gelatin and synthetic and semisynthetic polymers such as carbomer resins, cellulose ethers and carboxymethyl chitin. Solvents that may be used include but are not limited to Ringers solution, water, distilled water, dimethyl sulfoxide to 50% in water, propylene glycol (neat or in water), phosphate buffered saline, balanced salt solution, glycol and other conventional fluids.

Compositions which provide from about 10 mg to 1000 mg of the composition per unit dose are preferred and compositions may be formulated as tablets, lozenges, capsules, powders, aqueous or oily suspensions, syrups, elixirs, implants or aqueous solutions or in any other form and may be prepared by any conventional method. The nature of pharmaceutical composition employed will, of course, depend on the desired route of administration. The human dosage of the composition is in the range of 1.0 to 200 mg/kg/day and the preferred range is 1.0 to 50 mg/kg/day.

Systemic administration refers to oral, rectal, nasal, transdermal and parental (i.e., intramuscular, intraperitoneal, subcutaneous or intravenous). In accordance with good clinical practice, it is preferred to administer the composition at a dose that will produce good effects without causing undue harmful side effects. In one embodiment of this invention, the dose is one that will inhibit multiplication of cancer cells without causing harmful side effects. The composition may be administered either alone or as a mixture with other therapeutic agents.

The procedures mentioned below are either used alone or in combination to produce the derivatives.

PREPARATION OF BETULINIC ACID DERIVATIVES

EXAMPLE 1

Preparation of-o-benzoyl Derivatives

Substrate in organic base is treated with suitable benzoyl chloride for approximately 6–16 hours at an ambient temperature. Examples of benzoyl chloride that can be used are represented by general formula $R_n(Ar)CoCl$ wherein n=1 to 3, R=H, Cl, Br, F, $CF_3$, OH, $OCH_3$, $OC_2H_5$, CN, $NO_2$, $C_nH_{2n+1}$, where n=1 to 7 and Ar=$C_6H_5$, $C_6H_4$, $C_6H_3$ or $C_6H_2$. The reaction was worked up by addition of water and extraction with organic solvent. The organic layer was dried over anhydrous sodium sulfate, evaporated and residue crystallized to yield pure 3-o-benzoyl derivatives respectively. Examples of organic bases that can be used are pyridine, piperidine, and dimethylamino pyridine.

EXAMPLE 2

Preparation of 3-o-mesylate Derivatives

Substrate is dissolved in halogenated solvent and methane sulphonyl chloride is added slowly at 5–10° C. The mixture is stirred at an ambient temperature for 2–4 hours. The reaction mixture is worked up by washing the organic layer with water. The organic layer is dried over anhydrous sulfate, filtered, and evaporated to dryness to obtain a residue which was crystallized from acetonitrile to yield pure 3-o-mesylate derivative.

EXAMPLE 3

Preparation of 3-o-benzene Sulfonyl Derivative or its Benzene Substituted Derivative Substrate is dissolved in halogenated solvent. Benzene sulfonyl chloride or substituted benzene sulfonyl chloride and a few drops of pyridine is added at 5°–10° C. The mixture is stirred at ambient temperature for few hours to several hours, and is worked up as in Example 2. The 3-o-benzene sulfonyl derivative or its benzene substituted derivative is crystallized from alcoholic solvent to yield pure 3-o-benzene sulfonyl derivative.

EXAMPLE 4

Preparation of 3-phenyl Hydrazino or its Phenyl Substituted Derivative 3-phenylhydrazone or its phenyl substituted derivatives of betulinic acid or dihydrobetulinic acid is dissolved in glacial acetic acid and shaken under hydrogen atmosphere (50–70 psi) in presence of a platinum sponge catalyst for 3–5 hours. The reaction mixture is filtered, the mother liquour is evaporated under vacuum to remove glacial acetic acid and the residue is the crystallized from alcoholic solvent to yield pure 3-phenyl hydrazino or its phenyl substituted derivative. Alcoholic solvents used are methanol, ethanol or isopropanol.

EXAMPLE 5

Preparation of 3-N-Hydroxyethyl Derivative 3-oxo-derivative is dissolved in absolute alcoholic solvent such as methanol/ethanol and 15–20% alcoholic hydrochloric acid and 2-amino-ethanol are added and stirred at room temperature for 30–60 minutes. To this sodium cyanoborohydride is added and further stirred at room temperature for approximately 72 hours. The mixture is worked up by adding water followed by filtration of the solid to yield crude product, which was crystallized from alcohol to yield pure 3-N-hydroxyethyl derivative.

EXAMPLE 6

Preparation of 3-N-Benzylidene Derivative

3-Amino derivative is dissolved in alcoholic solvent, such as methanol/ethanol and benzaldehyde or substituted benzaldehyde derivative is added in the presence or absence of alkali carbonate, such as sodium or potassium carbonate. The mixture was stirred for few hours at ambient temperature to approximately 50° C. The reaction mixture was worked up by removing alcohol under vacuum and adding of water. The aqueous was layer either filtered or extracted with halogenated organic solvent, followed by evaporation to yield 3-N-benzylidene derivative.

EXAMPLE 7

Preparation of 3-oxo Derivative

The substrate was dissolved in the organic solvent and a conventional oxidizing agent was added under normal reaction conditions. The reaction was worked up to yield the corresponding 3-oxo derivatives in pure form.

EXAMPLE 8

Preparation of 3-oximino Derivatives

The 3-oxo derivative was dissolved in an alcoholic solvent. To this was added hydroxylamine hydrochloride and sodium acetate was added and the mixture was refluxed for a few hours preferably 6 to 12 hours. The reaction mixture was evaporated to dryness. The reaction was worked up as described in method I to yield crude 3-oximino derivatives, which was crystallized to yield the corresponding pure 3-oximino derivative.

EXAMPLE 9

Preparation of Phenylhydrazone of 3-oxo Derivative

Phenylhydrazine was added to 3-oxo derivative dissolved in alcoholic solvent and refluxed for 4–16 hours. The reaction was worked up as described in method I to yield the corresponding phenyl hydrazone derivative in pure form.

EXAMPLE 10

Preparation of C17 Carboxy Alkenoyl Derivative

Substrate in dry dimethyl formamide is stirred with sodium hydride at room temperature for an hour. Alkenoyl chloride $[(R)_2C=CHCOCl$; wherein R=H, $CH_3$ or $C_2H_5]$ was added and stirred at room temperature for few to several hours. Worked up by addition of water and extracting with halogenated organic solvent. The organic layer was dried over anhydrous sodium or magnesium sulphate, filtered and organic layer evaporated to yield a solid which was crystallized from alcoholic solvent to yield pure $C^{17}$ carboxyalkenoyl derivative.

EXAMPLE 11

Bromination of Aromatic Ring (a) To the betulinic-acid substrate (BA derivative) taken in trifluoroacetic acid, (b) add N-bromosuccinimide and a few drops of 10% aqueous sulphuric acid, (c) stir the reaction mixture at room temperature overnight, (d) add water and extract with ethylacetate, (e) wash the ethylacetate layer with aqueous bicarbonate solution, followed by water, (f) dry the organic layer over sodium sulphate, filter and evaporate it to dryness and crystallize the residue from alcoholic solvent to yield the pure bromo compound.

The above procedure can be deployed in compounds where aromatic nucleus is also deactivated.

EXAMPLE 12

Reduction of Aromatic Nitro Group to Amino Group (a) The betulinic acid derivative substrate is dissolved in methanol, (b) 10% Pd/c is added, followed by addition of sodium borohydride at an ambient temperature, (c) the reaction mixture is stirred for a few hours, (d) the reaction mixture is filtered, evaporated to dryness and worked up by adding water, extracting with an organic solvent, (e) drying the organic layer over anhydrous sodium sulphate, filtering and evaporating to dryness, (f) the residue of step (e) is crystallized from methanol or acetonitrile to yield pure amino compound.

EXAMPLE 13

Preparation of $C_{28}$ Carboxyl Derivative (Special Reference to Compounds of MJ-1155-RS, MJ-1161-RS and MJ-1163-RS a) Betulinic acid, Dihydrobetulinic acid or 2-Bromo-3-oxo-dihydrobetulinic acid is dissolved in dimethylformamide or halogenated organic solvent (preferably methylene chloride), (b) dicyclohexylcarbodimide and dimethylaminopyridine are added, (c) the reaction mixture is stirred at room temperature overnight, and (d) it is worked up by adding water, dried over anhydrous sodium sulphate, filtered and evaporated to dryness to yield a crude solid which is crystallized from alcohol to yield the corresponding pure derivative.

EXAMPLE 14

In vitro cytotoxic activity of novel betulinic acid derivatives was determined by performing the MTT cytotoxicity assay (Mosmann T., J. Immuno-logical Methods, 65:55

1983). Briefly, the cultured tumor cells were separately seeded in a 96-well culture plate and co-incubated with betulinic acid or its derivatives dissolved in methanol, dimethyl formamide, dimethyl sulfoxide or isopropyl alcohol with relevant controls at 37° C. in a $CO_2$ incubator. After 72 hours, the assay was terminated and percent cyotoxicities calculated. As shown in Table II, metabolic activity of leukemia cells (MOLT-4) was inhibited by active betulinic acid derivatives, i.e., an $ED_{50}$ value of about 0.34 to 2.0 μg/ml. The $ED_{50}$ value of active betulinic acid derivatives for lymphoma cells (U937) was in the range of 0.3 to 4.0, μg/ml, for human prostate (DU145), 0.4 to 4.0 μg/ml, for human colon (HT29) 0.35 to 4.0 μg/ml, for human larynx (HeP.2) 1.0 to 4.0 μg/ml, for human lung (L132) 0.50 to 4.0 μg/ml, and for ovarian cancer cells (PA-1) 0.50 to 4.0 μg/ml.

$R_1$ is H, Br, Cl, F or I;
$R_2$ is H and $R_3$ is $OCOC(CH_3)_3$, $OCO(CH_2)_mX$ (where m is 2 to 7 and X is H, Cl, Br, or F), $OCOCH_2C_6H_nY$ (where n is 2 to 4), $OCOC_{10}H_sY$, $OCOCH_2C_{10}H_sY$ (where s is 2 to 6) (where Y is H, Cl, Br, F, I, CN, $NO_2$, $NH_2$, $CF_3$, OH, $OCH_3$, $OC_2H_5$, $CHCl_2$ or $C_mH_{2m+1}$ (where m is 1 to 7)), $OCOC_6H_nZ^a$ (where n is 2 to 4 and $Z^a$ is CN, $NO_2$, $NH_2$, OH, $OCH_3$, $OC_2H_5$, $CHCl_2$ or $C_mH_{2m+1}$ (where m is 1 to 7)); $OCOC_6H_2Z^b$ (where $Z^b$ is Cl, Br, F, I, CN, $NO_2$, $NH_2$, $CF_3$, OH, $OCH_3$, $OC_2H_6$, $CHCl_2$ or $C_mH_{2m+1}$ (where m is 1 to 7)) $OCOC_6H_qY$ (where q is 0 or 1 and Y is H, Cl, Br, F, I, CN, $NO_2$, $NH_2$, $CF_3$, OH, $OCH_3$, $OC_2H_6$, $CHCl_2$ or $C_mH_{2m+1}$ (where m is 1 to 7)), $OCO(CH_2)_uNH_2$ (where u is 1 to 8), $OCOC_6H_4COOH$, $OCOC_6H_w(COOH)L$ (where w

TABLE II $ED_{50}$ VALUES (μg/ml) OF BETULINIC ACID DERIVATIVE

| Lymphoma U937 | Deriv | Leukemia MOLT-4 | Deriv. | Prostate DU 145 | Deriv | Lung L 132 | Deriv | Ovary PA-I | Deriv | Colon HT-29 | Deriv | Larynx Hep. 2 |
|---|---|---|---|---|---|---|---|---|---|---|---|---|
| BA | 0.7 | BA | 1.9 | BA | >10 | BA | 3.2 | BA | 17 | BA | 1.8 | BA | >10 |
| 751 | >4 | 751 | 0.65 | 751 | >10 | 751 | 5 | 751 | ND | 751 | ND | 751 | 7.0 |
| 789 | 1.4 | 789 | 2.0 | 789 | >10 | 789 | 6.5 | 789 | >4.0 | 789 | 1.4 | 789 | >10 |
| 807 | ND | 807 | 1.0 | 807 | >10 | 807 | <0.5 | 807 | 1.7 | 807 | ND | 807 | 4.0 |
| 829 | 0.5 | 829 | 0.4 | 829 | >10 | 829 | >4 | 829 | 0.5 | 829 | 1.3 | 829 | >10 |
| 878 | 0.4 | 878 | 1.6 | 978 | 9.9 | 878 | 0.8 | 878 | 3.5 | 878 | 1.75 | 878 | 2.25 |
| 912 | 1.2 | 912 | 1.0 | 912 | 8.5 | 912 | >4 | 912 | ND | 912 | 0.35 | 912 | 7.0 |
| 935 | 2.6 | 935 | 0.6 | 935 | 3.2 | 935 | 1.2 | 935 | ND | 935 | >10 | 935 | >10 |
| 937 | 1.2 | 937 | 0.9 | 937 | 2.5 | 937 | 1.1 | 937 | 1.6 | 937 | 1.7 | 937 | 5.9 |
| 939 | 5.7 | 939 | 1.4 | 939 | >10 | 939 | 2.7 | 939 | >4.0 | 939 | >10 | 939 | 4.0 |
| 940 | 0.8 | 940 | 0.4 | 940 | >4 | 940 | 2.6 | 940 | 3.8 | 940 | >10 | 940 | 5.4 |
| 942 | 2.2 | 942 | 0.5 | 942 | >10 | 942 | 4.0 | 942 | >4.0 | 942 | >10 | 942 | 10.0 |
| 943 | 3.2 | 943 | 1.6 | 943 | >4 | 943 | 4.0 | 943 | >4.0 | 943 | >10 | 943 | 2.0 |
| 998 | 1.6 | 998 | 1.9 | 998 | 2.2 | 998 | 2.5 | 998 | 1.2 | 998 | 4.0 | 998 | 3.0 |
| 1022 | 5.5 | 1022 | 1.8 | 1022 | >10 | 1022 | 4.7 | 1022 | 0.6 | 1022 | >10 | 1022 | 3.5 |
| 1025 | >10 | 1025 | 1.0 | 1025 | >4 | 1025 | 3.2 | 1025 | >4.0 | 1025 | >10 | 1025 | >10 |
| 1027 | 4.5 | 1027 | 2.0 | 1027 | 5.7 | 1027 | 7.0 | 1027 | >4.0 | 1027 | 7.2 | 1027 | 4.2 |
| 1065 | 1.9 | 1065 | 1.0 | 1065 | 2.5 | 1065 | 3.4 | 1065 | 1.4 | 1065 | 4.9 | 1065 | 2.6 |
| 1068 | >4 | 1068 | 1.5 | 1068 | >10 | 1068 | >4 | 1068 | >4.0 | 1068 | >10 | 1068 | >10 |
| 1073 | >4 | 1073 | 1.6 | 1073 | 2.5 | 1073 | >10 | 1073 | 3.3 | 1073 | >10 | 1073 | >10 |
| 1098 | 0.4 | 1098 | 0.5 | 1098 | 1.5 | 1098 | 1.3 | 1098 | 0.9 | 1098 | 2.6 | 1098 | 1.0 |
| 1101 | 1.2 | 1101 | 1.9 | 1101 | >10 | 1101 | 1.7 | 1101 | 3.5 | 1101 | >10 | 1101 | 1.6 |
| 1103 | 1.0 | 1103 | 1.9 | 1103 | >4 | 1103 | 4.0 | 1103 | 1.5 | 1103 | 10.0 | 1103 | 3.0 |
| 1104 | 1.1 | 1104 | 1.5 | 1104 | 2.0 | 1104 | 5.9 | 1104 | 0.8 | 1104 | 3.5 | 1104 | 1.7 |
| 1108 | 1.0 | 1108 | 1.5 | 1108 | >4 | 1108 | 4.6 | 1108 | 1.3 | 1108 | >10 | 1108 | 1.7 |
| 1138 | 1.1 | 1138 | 2.0 | 1138 | >10 | 1138 | 7.0 | 1138 | 1.3 | 1138 | >10 | 1138 | 2.0 |
| 1155 | >10 | 1155 | 1.1 | 1155 | >10 | 1155 | >10 | 1155 | >4.0 | 1155 | >10 | 1155 | >10 |
| 1161 | 0.3 | 1161 | 0.34 | 1161 | 0.4 | 1161 | 3.5 | 1161 | 1.2 | 1161 | 3.5 | 1161 | 1.4 |
| 1163 | 3.8 | 1163 | 1.6 | 1163 | 6.0 | 1163 | 6.5 | 1163 | >4.0 | 1163 | 7.3 | 1163 | 5.0 |

What is claimed is:
1. A betulinic acid derivative of formula 2

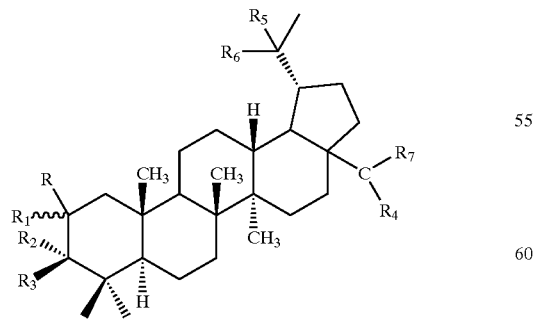

wherein R, $R_1$, $R_2$, $R_3$, $R_4$, $R_5$, $R_6$ and $R_7$ independently or in combination represent the following groups:
R is H;

is 2 or 3, and L is H, Cl, Br, F, $NO_2$ or $NH_2$), $OCOCHQQ_1$, (where Q is H, $CH_3$ or Ph and $Q_1$ is OH, Cl, Br or $OCOCH_3$), $OCOCH=C(X')^2$ (where X' is H, $CH_3$ or $C_2H_5$), O—CO—C(Br)=CHCOOH,

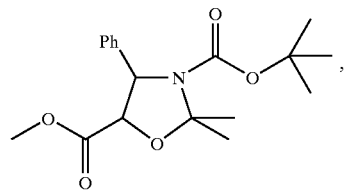

—OOCCH(OH)CH(Ph)A (where A is $NH_2$, or $NHC_6H_nZ'$ (where n is 2 to 4 and Z' is H, Cl, F or Br)),
$R_7$ is O and $R_4$ is OM (where M is $Na^+$, $K^+$, $Li^+$), OB (where B is H, $CH_3$, $C_2H_5$, $C_3H_7$, or $C_4H_9$), $O(CH_2)_t$ $COD'$ (where t is 1 to 3 and D' is OH, $OCH_3$, $OC_2H_5$, Cl, CN, $N_3$, $NH_2$), $OCH_2CH_2OE'$ (where E' is H, $CH_3$, $C_2H_5$, or $COCH_3$), $OCOCH=C(X')_2$ (where X' is H, $CH_3$ or $C_2H_5$), $OCO(CH_2)_xZ'$ (where x is 1 to 16 and Z' is H, Cl, F or Br), $OCOC_6H_qF'$ (where q is 0 to 4), $OCOCH_2C_6H_nF'$ (where n is 2 to 4) (F' is H, Cl, Br, F, I, CN, $NO_2$, $CF_3$, $CHCl_2$, OH, $OCH_3$, $OC_2H_5$ or $C_mH_{2m+1}$ (where m is 1 to 7)), $OCH_2CHO$, $OCH_2CH=NOG'$, $OCH_2CH_2NHOG'$ (where G' is H, $CH_3$, $SO_2C_6H_4CH_3$, $OCOCH_3$, $OCOC_6H_5$, phenyl or benzyl substituted derivatives), $OCH_2CH=NNHC_6H_nY$, $OCH_2CH_2NHNHC_6H_nY$ (where n is 2 to 4), $OCH_2CH=NNHC_{10}H_sY$ (where s is 2 to 6), $OCH_2CH_2CH_2NHNHC_{10}H_mY$ (where Y is H, Cl, Br, F, I, CN, $CF_3$, $CHCl_2$, $NO_2$, $NH_2$, OH, $OCH_3$, $OC_2H_5$ or $C_mH_{2m+1}$ (where m is 1 to 7)), $OCH_2CH_2N(H')_2$ (where H' is H, $CH_3$, $C_2H_5$, $C_3H_7$, $C_4H_9$, $C_6H_5$, $C_6H_5CH_2$ or its substituted derivative wherein the substituent is selected from Cl, Br, CN, F, I, $NO_2$, $NH_2$, $CF_3$, $CHCl_2$, OH, $OCH_3$, $OC_2H_5$ or $C_mH_{2m+1}$ (where m is 1 to 7)), O-(3deoxybetulinic acid), O-(3-deoxydihydrobetulinic acid), or O-(2-Bromo-3-oxo-28-oyl-lupane);

$R_5$ is H or Br;

$R_6$ is $CH_3$, or $CH_2Br$.

2. A betulinic acid derivative of structure (3)

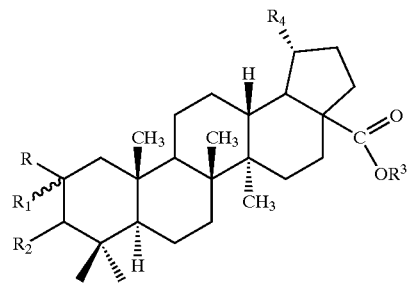

where

R is H, $R_1$ is H or Br $R_2$—$OCOCH(OCOCH_3)CH_3$, $OCOCH(OCOCH_3)C_6H_5$, —$OCOC_6H_4(C_5H_{11})(4)$, —$OCOCH_2C_6H_3(OCH_3)_2(2,5)$, —$OCOC_6H_4(C_7H_{15})(4)$, —$OCOCH_2C_6H_3(OCH_3)_2(3,4)$, —$OCOC_6H_4(OC_2H_5)(4)$, —$OCOCH_2C_6H_3Br(3)(OCH_3)_2(2,5)$, —$OCO(CH_2)_3NH_2$, —$OCOC_6H_3(OCH_3)_2(2,4)$, —$OCOC_6H_4(C_6H_5)(4)$, —$OCOCCl(C_6H_5)(2)$, —$OCOC_6H_3(OCH_3)_2(3,4)$, —$OCOC(CH_3)=C(CH_3)COOH$, $OCOCClF_2$, —$OCOC_6H_4(CHCl_2)(3)$, $OCOC_6H_2COOH(2)Cl_2(3,6)$, $OCOC_6H_2Br(6)F_2(2,4)$, —O-Cyclopropanoyl, —O-Cyclobutanoyl, —O-Cyclohexanoyl, —O-Morpholinoyl, or

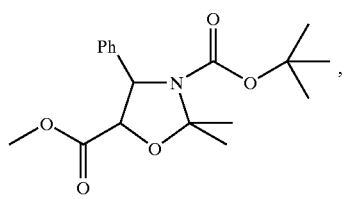

$R_3$ is H, $CH_2COOCH_3$, —$CH_2COOH$, —$CH_2CH_2COOCH_3$, —$COCH=CH_2$, 3-Deoxydihydrobetulinic acid ($C_3\rightarrow$), 3-Deoxybetulinic acid ($C_3\rightarrow$), or 2-Bromo-3-oxo-28-oyl lupane and $R_4$ is $CH_2=C(CH_3)$ or $BrCH_2C(Br)CH_3$.

3. A betulinic acid derivative of formula 2

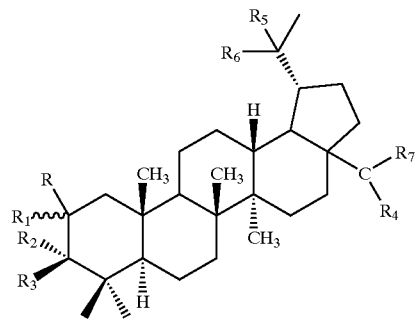

wherein

R is H, $R_1$ is Br, Cl, F or I, $R_2$ is H, $R_3$ is $OCOCH_3$, $OCO(CH_2)_mCH_3$ (where m is 1 or 2), $OCOC_6H_nY$ (where n is 4; Y is H, Cl, Br, F, I, $OCH_3$, $NO_2$, $C_mH_{2m+1}$ (m is 1));

$R_7$ is O and $R_4$ is OM (where M is $Na^+$, $K^+$, $Li^+$), OB (where B is $CH_3$, $C_2H_5$, $C_3H_7$, or $C_4H_9$), $O(CH_2)_tCOD'$ (where t is 1 to 3 and D' is OH, $OCH_3$, $OC_2H_6$, Cl, CN, $N_3$, or $NH_2$), $OCH_2CH_2OE'$ (where E' is H, $CH_3$, $C_2H_5$, or $COCH_3$), $OCOCH=C(X')_2$ (where X' is H, $CH_3$, or $C_2H_5$), $OCO(CH_2)_xZ'$ (where x is 1 to 16 and Z' is H, Cl, F or Br), $OCOC_6H_qF'$ (where q is 0 to 4), $OCOCH_2C_6H_nF'$ (where n is 2 to 4) (F' is H, Cl, Br, F, I, CN, $NO_2$, $CF_3$, $CHCl_2$, OH, $OCH_3$, $OC_2H_5$ or $C_mH_{2m+1}$ (where m is 1 to 7)), $OCH_2CHO$, $OCH_2CH=NOG'$, $OCH_2CH_2NHOG'$ (where G' is H, $CH_3$, $SO_2C_6H_4CH_3$, $OCOCH_3$, $OCOC_6H_5$, phenyl or benzyl substituted derivatives), $OCH_2CH=NNHC_6H_nY$, $OCH_2CH_2NHNHC_6H_nY$ (where n is 2 to 4), $OCH_2CH=NNHC_{10}H_sY$ (where s is 2 to 6), $OCH_2CH_2CH_2NHNHC_{10}H_mY$ (where Y is H, Cl, Br, F, I, CN, $CF_3$, $CHCl_2$, $NO_2$, $NH_2$, OH, $OCH_3$, $OC_2H_5$ or $C_mH_{2m+1}$ (where m is 1 to 7)), $OCH_2CH_2N(H')_2$ (where H' is H, $CH_3$, $C_2H_5$, $C_3H_7$, $C_4H_9$, $C_6H_5$, $C_6H_5CH_2$ or its substituted derivative wherein the substituent is selected from Cl, Br, CN, F, I, $NO_2$, $NH_2$, $CF_3$, $CHCl_2$, OH, $OCH_3$, $OC_2H_5$ or $C_mH_{2m+1}$ (where m is 1 to 7)), O-(3-deoxybetulinic acid), O-(3-deoxydihydrobetulinic acid), or O-(2-Bromo-3-oxo-28-oyl-lupane);

$R_5$ is H or Br; and $R_6$ is $CH_3$, or $CH_2Br$.

4. A betulinic acid derivative of formula 2

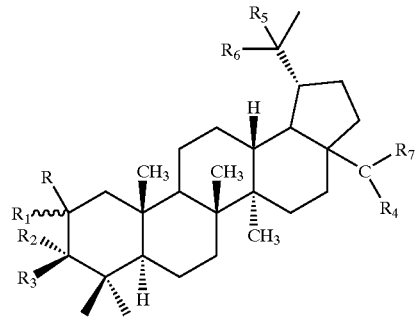

wherein

R is H;

$R_1$ is H, Br, Cl, F or I;

$R_2$ is H
and $R_3$ is $OCOCH_2C(Y')^2COOH$ (Y' is H or $CH_3$); $OCO(CH_2)_pCOOH$ (p is 2 and 3);
$R_7$ is O and $R_4$ is OM (where M is $Na^+$, $K^+$, $Li^+$), OB (where B is H, $CH_3$, $C_2H_5$, $C_9H_7$, or $C_4H_9$), $O(CH_2)_tCOD'$ (where t is 1 to 3 and D' is OH, $OCH_3$, $OC_2H_5$, Cl, CN, $N_3$, $NH_2$), $OCH_2CH_2OE'$ (where E' is H, $CH_3$, $C_2H_5$, or $COCH_3$), $OCOCH=C(X')^2$ (where X' is H, $CH_3$ or $C_2H_5$), $OCO(CH_2)_xZ'$ (where x is 1 to 16 and Z' is H, Cl, F or Br), $OCOC_6H_qF'$ (where q is 0 to 4), $OCOCH_2C_6H_nF'$ (where n is 2 to 4) (F' is H, Cl, Br, F, I, CN, $NO_2$, $CF_3$, $CHCl_2$, OH, $OCH_3$, $OC_2H_5$ or $C_mH_{2m+1}$ (where m is 1 to 7)), $OCH_2CHO$, $OCH_2CH=NOG'$, $OCH_2CH_2NHOG'$ (where G' is H, $CH_3$, $SO_2C_6H_4CH_3$, $OCOCH_3$, $OCOC_6H_5$, phenyl or benzyl substituted derivatives), $OCH_2CH=NNHC_6H_nY$, $OCH_2CH_2NHNHC_6H_nY$ (where n is 2 to 4), $OCH_2CH=NNHC_{10}H_sY$ (where s is 2 to 6), $OCH_2CH_2CH_2NHNHC_{10}H_mY$ (where Y is H, Cl, Br, F, I, CN, $CF_3$, $CHCl_2$, $NO_2$, $NH_2$, OH, $OCH_3$, $OC_2H_5$ or $C_mH_{2m+1}$ (where m is 1 to 7)), $OCH_2CH_2N(H')^2$ (where H' is H, $CH_3$, $C_2H_5$, $C_3H_7$, $C_4H_9$, $C_6H_5$, $C_6H_5CH_2$ or its substituted derivative wherein the substituent is selected from Cl, Br, CN, F, I, $NO_2$, $NH_2$, $CF_3$, $CHCl_2$, OH, $OCH_3$, $OC_2H_5$ or $C_mH_{2m+1}$ (where m is 1 to 7)), O-(3deoxybetulinic acid), O-(3-deoxydihydrobetulinic acid), or O-(2-Bromo-3-oxo-28oyl-lupane);
$R_5$ is H or Br;
$R_6$ is $CH_3$, or $CH_2Br$.
5. A betulinic acid derivative of structure (3)

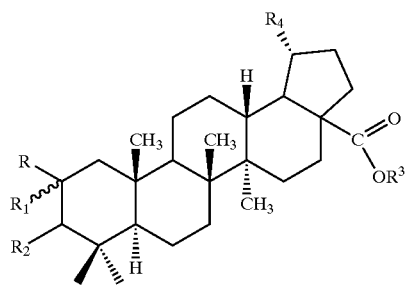

where
R is H,
$R_1$ is H or Br
$R_2$ is —$OCOCH(OCOCH_3)CH_3$, —$OCOCH(OCOCH_3)C_6H_5$, —$OCOC_6H_4(C_5H_{11})(4)$, —$OCOCH_2C_6H_3(OCH_3)_2(2,5)$, —$OCOC_6H_4(C_7H_{15})(4)$, —$OCOCH_2C_6H_3(OCH_3)_2(3,4)$, —$OCOC_6H_4(OC_2H_5)(4)$, —$OCOCH_2C_6H_2Br(3)(OCH_3)_2(2,5)$, —$OCO(CH_2)_3NH_2$, $OCOC_6H_3(OCH_3)_2(2,4)$, —$OCOC_6H_4(C_6H_5)(4)$, $OCOCCl(C_6H_5)(2)$, —$OCOC_6H_3(OCH_3)_2(3,4)$, —$OCOC(CH_3)=C(CH_3)COOH$, $OCOCClF_2$, —$OCOC_6H_4(CHCl_2)(3)$, $OCOC_6H_2COOH(2)Cl_2(3,6)$, $OCOC_6H_2Br(6)F_2(2,4)$ $OCOC_6H_2F_3(2,3,4)$, $OCOC_6H_2F_3(2,3,5)$, $OCOC_6H_2F_3(2,3,6)$, —O-Cyclopropanoyl, —O-Cyclobutanoyl, —O-Cyclohexanoyl, —O-Morpholinoyl, or

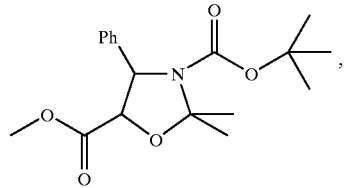, $R^3$ is hydrogen and
$R_4$ is $CH_2=C-CH_3$, or $CH(CH_3)_2$ or $BrCH_2C(Br)CH_3$.
6. A composition comprising a betulinic acid derivative of claim 1, and a pharmaceutically acceptable additive, carrier, diluent, solvent, filler, lubricant, excipient, binder or stabilizer.
7. The composition as claimed in claim 6, which provides 10 mg to 1000 mg per unit dose of betulinic acid derivative.
8. A composition comprising a betulinic acid derivative of claim 2, and a pharmaceutically acceptable additive, carrier, diluent, solvent, filler, lubricant, excipient, binder or stabilizer.
9. The composition as claimed in claim 8, which provides 10 mg to 1000 mg per unit dose of betulinic acid derivative.
10. A composition comprising a betulinic acid derivative of claim 3, and a pharmaceutically acceptable additive, carrier, diluent, solvent, filler, lubricant, excipient, binder or stabilizer.
11. The composition as claimed in claim 10, which provides 10 mg to 1000 mg per unit dose of betulinic acid derivative.
12. A composition comprising a betulinic acid derivative of claim 4, and a pharmaceutically acceptable additive, carrier, diluent, solvent, filler, lubricant, excipient, binder or stabilizer.
13. The composition as claimed in claim 12, which provides 10 mg to 1000 mg per unit dose of betulinic acid derivative.
14. A composition comprising a betulinic acid derivative of claim 5, and a pharmaceutically acceptable additive, carrier, diluent, solvent, filler, lubricant, excipient, binder or stabilizer.
15. The composition as claimed in claim 14 which provides 10 mg to 1000 mg per unit dose of betulinic acid derivative.

* * * * *

UNITED STATES PATENT AND TRADEMARK OFFICE
CERTIFICATE OF CORRECTION

PATENT NO. : 6,670,345 B1  
DATED : December 30, 2003  
INVENTOR(S) : Sunder Ramadoss et al.

It is certified that error appears in the above-identified patent and that said Letters Patent is hereby corrected as shown below:

<u>Title page, Item [54] and Column 1, line 2,</u>  
"INHABITING" should read -- INHIBITING --.

Signed and Sealed this

Twenty-fourth Day of February, 2004

JON W. DUDAS  
*Acting Director of the United States Patent and Trademark Office*